US009133253B2

(12) United States Patent
Legler et al.

(10) Patent No.: US 9,133,253 B2
(45) Date of Patent: Sep. 15, 2015

(54) RICIN VACCINE AND METHODS OF MAKING THEREOF

(75) Inventors: Patricia M. Legler, Derwood, MD (US); Jaimee R. Compton, Washington, DC (US); Charles B. Millard, Frederick, MD (US); Mark A. Olson, Middletown, MD (US)

(73) Assignee: The United States of America as Represented by the Secretary of the Army, Washington, DC (US)

(*) Notice: Subject to any disclaimer, the term of this patent is extended or adjusted under 35 U.S.C. 154(b) by 220 days.

(21) Appl. No.: 13/634,414

(22) PCT Filed: Apr. 21, 2011

(86) PCT No.: PCT/US2011/033486
§ 371 (c)(1),
(2), (4) Date: Oct. 16, 2013

(87) PCT Pub. No.: WO2012/011992
PCT Pub. Date: Jan. 26, 2012

(65) Prior Publication Data
US 2013/0295101 A1    Nov. 7, 2013

Related U.S. Application Data

(60) Provisional application No. 61/343,944, filed on Apr. 22, 2010.

(51) Int. Cl.
*C07K 14/415* (2006.01)
*C07K 16/16* (2006.01)
*A61K 38/00* (2006.01)

(52) U.S. Cl.
CPC .............. *C07K 14/415* (2013.01); *C07K 16/16* (2013.01); *A61K 38/00* (2013.01); *C07K 2317/34* (2013.01)

(58) Field of Classification Search
CPC .. C07K 16/16; C07K 14/415; C07K 2317/34; A61K 38/00
See application file for complete search history.

(56) References Cited

U.S. PATENT DOCUMENTS

| | | | |
|---|---|---|---|
| 6,869,787 B2 | 3/2005 | Olson | |
| 6,960,652 B2* | 11/2005 | Vitetta et al. | 530/350 |
| 7,351,435 B2 | 4/2008 | Wannemacher | |
| 7,407,935 B2 | 8/2008 | Olson | |
| 2003/0181665 A1* | 9/2003 | Olson et al. | 530/370 |
| 2006/0009619 A1 | 1/2006 | Olson | |

FOREIGN PATENT DOCUMENTS

WO    WO03072018    * 9/2003

OTHER PUBLICATIONS

International Search Report received in PCT/US2011/033486, mailed Mar. 26, 2012.
Carra, J.H. et al. (2007) "Improved Formulation of a Recombinant Ricin A-Chain Vaccine Increases it Stability and and Effective Antigenicity" Vaccine, 25: 4149-4158.
IDS and PTO 1449 Forms from US 6,869,787, issued Mar. 22, 2005, and US 7,407,935, issued Aug. 5, 2008.
IDS and PTO 1449 Forms from US 7,351,435, issued Apr. 1, 2008.

* cited by examiner

*Primary Examiner* — Phuong Huynh
(74) *Attorney, Agent, or Firm* — Elizabeth Arwine, Esq.; Suzannah K. Sundby, Esq.; Canady + Lortz LLP

(57) ABSTRACT

Disclosed herein ricin toxin A chain polypeptides having an engineered disulfide bond ((SS)RTA) and compositions thereof. The disclosed (SS)RTA polypeptides retain the immunological epitope of wild type RTA, lack detectable N-glycosidase activity or exhibit reduced N-glycosidase activity as compared to controls, and exhibit increased solubility, thermal stability and a lower tendency to self-aggregate as compared to RTA 198 and/or RTA 1-33/44-198. Also disclosed are immunogenic compositions that may be used to immunize a subject against ricin intoxication. Methods of immunizing against, treating, inhibiting, reducing and/and preventing ricin intoxication are disclosed.

17 Claims, 3 Drawing Sheets

SEQUENCE LISTING

<160> NUMBER OF SEQ ID NOS: 28

<210> SEQ ID NO 1
<211> LENGTH: 267
<212> TYPE: PRT
<213> ORGANISM: Ricinus communis

<400> SEQUENCE: 1

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Thr Gly Ala Asp Val Arg His Glu Ile Pro Val Leu Pro Asn Arg
        35                  40                  45

Val Gly Leu Pro Ile Asn Gln Arg Phe Ile Leu Val Glu Leu Ser Asn
    50                  55                  60

His Ala Glu Leu Ser Val Thr Leu Ala Leu Asp Val Thr Asn Ala Tyr
65                  70                  75                  80

Val Val Gly Tyr Arg Ala Gly Asn Ser Ala Tyr Phe Phe His Pro Asp
                85                  90                  95

Asn Gln Glu Asp Ala Glu Ala Ile Thr His Leu Phe Thr Asp Val Gln
            100                 105                 110

Asn Arg Tyr Thr Phe Ala Phe Gly Gly Asn Tyr Asp Arg Leu Glu Gln
        115                 120                 125

Leu Ala Gly Asn Leu Arg Glu Asn Ile Glu Leu Gly Asn Gly Pro Leu
    130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
                165                 170                 175

Glu Ala Ala Arg Phe Gln Tyr Ile Glu Gly Glu Met Arg Thr Arg Ile
            180                 185                 190

Arg Tyr Asn Arg Arg Ser Ala Pro Asp Pro Ser Val Ile Thr Leu Glu
        195                 200                 205

Asn Ser Trp Gly Arg Leu Ser Thr Ala Ile Gln Glu Ser Asn Gln Gly
    210                 215                 220

Ala Phe Ala Ser Pro Ile Gln Leu Gln Arg Arg Asn Gly Ser Lys Phe
225                 230                 235                 240

Ser Val Tyr Asp Val Ser Ile Leu Ile Pro Ile Ile Ala Leu Met Val
                245                 250                 255

Tyr Arg Cys Ala Pro Pro Pro Ser Ser Gln Phe
            260                 265

<210> SEQ ID NO 2
<211> LENGTH: 198
<212> TYPE: PRT
<213> ORGANISM: Artificial Sequence
<220> FEATURE:
<223> OTHER INFORMATION: RTA 198 based on Ricinus communis

<400> SEQUENCE: 2

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Thr Gly Ala Asp Val Arg His Glu Ile Pro Val Leu Pro Asn Arg
        35                  40                  45

Val Gly Leu Pro Ile Asn Gln Arg Phe Ile Leu Val Glu Leu Ser Asn
 50                  55                  60

His Ala Glu Leu Ser Val Thr Leu Ala Leu Asp Val Thr Asn Ala Tyr
 65                  70                  75                  80

Val Val Gly Tyr Arg Ala Gly Asn Ser Ala Tyr Phe Phe His Pro Asp
                 85                  90                  95

Asn Gln Glu Asp Ala Glu Ala Ile Thr His Leu Phe Thr Asp Val Gln
            100                 105                 110

Asn Arg Tyr Thr Phe Ala Phe Gly Gly Asn Tyr Asp Arg Leu Glu Gln
            115                 120                 125

Leu Ala Gly Asn Leu Arg Glu Asn Ile Glu Leu Gly Asn Gly Pro Leu
            130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
                165                 170                 175

Glu Ala Ala Arg Phe Gln Tyr Ile Glu Gly Glu Met Arg Thr Arg Ile
                180                 185                 190

Arg Tyr Asn Arg Arg Ser
            195

<210> SEQ ID NO 3
<211> LENGTH: 188
<212> TYPE: PRT
<213> ORGANISM: Artificial Sequence
<220> FEATURE:
<223> OTHER INFORMATION: RTA 1-33/44-198 based on Ricinus communis

<400> SEQUENCE: 3

Ile Phe Pro Lys Gln Tyr Pro Ile Ile Asn Phe Thr Thr Ala Gly Ala
 1               5                  10                  15

Thr Val Gln Ser Tyr Thr Asn Phe Ile Arg Ala Val Arg Gly Arg Leu
                 20                  25                  30

Thr Val Leu Pro Asn Arg Val Gly Leu Pro Ile Asn Gln Arg Phe Ile
             35                  40                  45

Leu Val Glu Leu Ser Asn His Ala Glu Leu Ser Val Thr Leu Ala Leu
 50                  55                  60

Asp Val Thr Asn Ala Tyr Val Val Gly Tyr Arg Ala Gly Asn Ser Ala
 65                  70                  75                  80

Tyr Phe Phe His Pro Asp Asn Gln Glu Asp Ala Glu Ala Ile Thr His
                 85                  90                  95

Leu Phe Thr Asp Val Gln Asn Arg Tyr Thr Phe Ala Phe Gly Gly Asn
            100                 105                 110

Tyr Asp Arg Leu Glu Gln Leu Ala Gly Asn Leu Arg Glu Asn Ile Glu
            115                 120                 125

Leu Gly Asn Gly Pro Leu Glu Glu Ala Ile Ser Ala Leu Tyr Tyr Tyr
            130                 135                 140

Ser Thr Gly Gly Thr Gln Leu Pro Thr Leu Ala Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Ile Arg Tyr Asn Arg Arg Ser
            180                 185

<210> SEQ ID NO 4

```
<211> LENGTH: 64
<212> TYPE: PRT
<213> ORGANISM: Artificial Sequence
<220> FEATURE:
<223> OTHER INFORMATION: (SS)RTA sequence based on Ricinus communis
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid

<400> SEQUENCE: 4

Xaa Xaa Gly Leu Pro Ile Asn Gln Arg Phe Ile Leu Val Glu Leu Ser
1               5                   10                  15

Asn His Ala Glu Leu Ser Val Thr Leu Ala Xaa Xaa Xaa Xaa Asn Ala
            20                  25                  30

Tyr Val Val Gly Tyr Arg Ala Gly Asn Ser Xaa Tyr Phe Phe His Pro
        35                  40                  45

Asp Asn Gln Xaa Asp Ala Glu Ala Ile Thr His Leu Phe Thr Asp Xaa
    50                  55                  60

<210> SEQ ID NO 5
<211> LENGTH: 48
<212> TYPE: PRT
<213> ORGANISM: Artificial Sequence
<220> FEATURE:
<223> OTHER INFORMATION: Second sequence based on Ricinus communis

<400> SEQUENCE: 5

Met Ile Phe Pro Lys Gln Tyr Pro Ile Ile Asn Phe Thr Thr Ala Gly
1               5                   10                  15

Ala Thr Val Gln Ser Tyr Thr Asn Phe Ile Arg Ala Val Arg Gly Arg
            20                  25                  30

Leu Thr Thr Gly Ala Asp Val Arg His Glu Ile Pro Val Leu Pro Asn
        35                  40                  45

<210> SEQ ID NO 6
<211> LENGTH: 47
<212> TYPE: PRT
<213> ORGANISM: Artificial Sequence
<220> FEATURE:
<223> OTHER INFORMATION: Second sequence based on Ricinus communis

<400> SEQUENCE: 6

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Thr Gly Ala Asp Val Arg His Glu Ile Pro Val Leu Pro Asn
        35                  40                  45
```

-continued

```
<210> SEQ ID NO 7
<211> LENGTH: 47
<212> TYPE: PRT
<213> ORGANISM: Artificial Sequence
<220> FEATURE:
<223> OTHER INFORMATION: Second sequence based on Ricinus communis

<400> SEQUENCE: 7

Met Val Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Thr Gly Ala Asp Val Arg His Glu Ile Pro Val Leu Pro Asn
        35                  40                  45

<210> SEQ ID NO 8
<211> LENGTH: 38
<212> TYPE: PRT
<213> ORGANISM: Artificial Sequence
<220> FEATURE:
<223> OTHER INFORMATION: Second sequence based on Ricinus communis

<400> SEQUENCE: 8

Met Ile Phe Pro Lys Gln Tyr Pro Ile Ile Asn Phe Thr Thr Ala Gly
1               5                   10                  15

Ala Thr Val Gln Ser Tyr Thr Asn Phe Ile Arg Ala Val Arg Gly Arg
            20                  25                  30

Leu Thr Val Leu Pro Asn
        35

<210> SEQ ID NO 9
<211> LENGTH: 37
<212> TYPE: PRT
<213> ORGANISM: Artificial Sequence
<220> FEATURE:
<223> OTHER INFORMATION: Second sequence based on Ricinus communis

<400> SEQUENCE: 9

Met Val Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Val Leu Pro Asn
        35

<210> SEQ ID NO 10
<211> LENGTH: 37
<212> TYPE: PRT
<213> ORGANISM: Artificial Sequence
<220> FEATURE:
<223> OTHER INFORMATION: Second sequence based on Ricinus communis

<400> SEQUENCE: 10

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Val Leu Pro Asn
        35

<210> SEQ ID NO 11
<211> LENGTH: 34
<212> TYPE: PRT
```

```
<213> ORGANISM: Artificial Sequence
<220> FEATURE:
<223> OTHER INFORMATION: Second sequence based on Ricinus communis

<400> SEQUENCE: 11

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Val

<210> SEQ ID NO 12
<211> LENGTH: 87
<212> TYPE: PRT
<213> ORGANISM: Artificial Sequence
<220> FEATURE:
<223> OTHER INFORMATION: Third sequence based on Ricinus communis

<400> SEQUENCE: 12

Gln Asn Arg Tyr Thr Phe Ala Phe Gly Gly Asn Tyr Asp Arg Leu Glu
1               5                   10                  15

Gln Leu Ala Gly Asn Leu Arg Glu Asn Ile Glu Leu Gly Asn Gly Pro
            20                  25                  30

Leu Glu Glu Ala Ile Ser Ala Leu Tyr Tyr Tyr Ser Thr Gly Gly Thr
        35                  40                  45

Gln Leu Pro Thr Leu Ala Arg Ser Phe Ile Ile Cys Ile Gln Met Ile
    50                  55                  60

Ser Glu Ala Ala Arg Phe Gln Tyr Ile Glu Gly Glu Met Arg Thr Arg
65                  70                  75                  80

Ile Arg Tyr Asn Arg Arg Ser
                85

<210> SEQ ID NO 13
<211> LENGTH: 88
<212> TYPE: PRT
<213> ORGANISM: Artificial Sequence
<220> FEATURE:
<223> OTHER INFORMATION: Third sequence based on Ricinus communis

<400> SEQUENCE: 13

Gln Asn Arg Tyr Thr Phe Ala Phe Gly Gly Asn Tyr Asp Arg Leu Glu
1               5                   10                  15

Gln Leu Ala Gly Asn Leu Arg Glu Asn Ile Glu Leu Gly Asn Gly Pro
            20                  25                  30

Leu Glu Glu Ala Ile Ser Ala Leu Tyr Tyr Tyr Ser Thr Gly Gly Thr
        35                  40                  45

Gln Leu Pro Thr Leu Ala Arg Ser Phe Ile Ile Cys Ile Gln Met Ile
    50                  55                  60

Ser Glu Ala Ala Arg Phe Gln Tyr Ile Glu Gly Glu Met Arg Thr Arg
65                  70                  75                  80

Ile Arg Tyr Asn Arg Arg Ser Ala
                85

<210> SEQ ID NO 14
<211> LENGTH: 198
<212> TYPE: PRT
<213> ORGANISM: Artificial Sequence
<220> FEATURE:
<223> OTHER INFORMATION: (SS)RTA 198 based on Ricinus communis
<220> FEATURE:
<221> NAME/KEY: misc_feature
```

<222> LOCATION: (48)..(49)
<223> OTHER INFORMATION: Xaa can be any naturally occurring amino acid
<220> FEATURE:
<221> NAME/KEY: misc_feature
<222> LOCATION: (74)..(77)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid

<400> SEQUENCE: 14

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Thr Gly Ala Asp Val Arg His Glu Ile Pro Val Leu Pro Asn Xaa
        35                  40                  45

Xaa Gly Leu Pro Ile Asn Gln Arg Phe Ile Leu Val Glu Leu Ser Asn
50                  55                  60

His Ala Glu Leu Ser Val Thr Leu Ala Xaa Xaa Xaa Asn Ala Tyr
65                  70                  75                  80

Val Val Gly Tyr Arg Ala Gly Asn Ser Xaa Tyr Phe Phe His Pro Asp
            85                  90                  95

Asn Gln Xaa Asp Ala Glu Ala Ile Thr His Leu Phe Thr Asp Xaa Gln
        100                 105                 110

Asn Arg Tyr Thr Phe Ala Phe Gly Gly Asn Tyr Asp Arg Leu Glu Gln
    115                 120                 125

Leu Ala Gly Asn Leu Arg Glu Asn Ile Glu Leu Gly Asn Gly Pro Leu
130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
            165                 170                 175

Glu Ala Ala Arg Phe Gln Tyr Ile Glu Gly Glu Met Arg Thr Arg Ile
        180                 185                 190

Arg Tyr Asn Arg Arg Ser
        195

<210> SEQ ID NO 15
<211> LENGTH: 188
<212> TYPE: PRT
<213> ORGANISM: Artificial Sequence
<220> FEATURE:
<223> OTHER INFORMATION: (SS)RTA 1-33/44-198 based on Ricinus communis
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (64)..(67)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid

```
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 15

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Val Leu Pro Asn Xaa Xaa Gly Leu Pro Ile Asn Gln Arg Phe Ile
        35                  40                  45

Leu Val Glu Leu Ser Asn His Ala Glu Leu Ser Val Thr Leu Ala Xaa
    50                  55                  60

Xaa Xaa Xaa Asn Ala Tyr Val Val Gly Tyr Arg Ala Gly Asn Ser Xaa
65                  70                  75                  80

Tyr Phe Phe His Pro Asp Asn Gln Xaa Asp Ala Glu Ala Ile Thr His
                85                  90                  95

Leu Phe Thr Asp Xaa Gln Asn Arg Tyr Thr Phe Ala Phe Gly Gly Asn
            100                 105                 110

Tyr Asp Arg Leu Glu Gln Leu Ala Gly Asn Leu Arg Glu Asn Ile Glu
        115                 120                 125

Leu Gly Asn Gly Pro Leu Glu Glu Ala Ile Ser Ala Leu Tyr Tyr Tyr
    130                 135                 140

Ser Thr Gly Gly Thr Gln Leu Pro Thr Leu Ala Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Ile Arg Tyr Asn Arg Arg Ser
            180                 185

<210> SEQ ID NO 16
<211> LENGTH: 199
<212> TYPE: PRT
<213> ORGANISM: Artificial Sequence
<220> FEATURE:
<223> OTHER INFORMATION: (SS)RTA based on Ricinus communis
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (75)..(78)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid

<400> SEQUENCE: 16

Met Ile Phe Pro Lys Gln Tyr Pro Ile Ile Asn Phe Thr Thr Ala Gly
1               5                   10                  15
```

```
Ala Thr Val Gln Ser Tyr Thr Asn Phe Ile Arg Ala Val Arg Gly Arg
            20                  25                  30

Leu Thr Thr Gly Ala Asp Val Arg His Glu Ile Pro Val Leu Pro Asn
        35                  40                  45

Xaa Xaa Gly Leu Pro Ile Asn Gln Arg Phe Ile Leu Val Glu Leu Ser
    50                  55                  60

Asn His Ala Glu Leu Ser Val Thr Leu Ala Xaa Xaa Xaa Asn Ala
65                  70                  75                  80

Tyr Val Val Gly Tyr Arg Ala Gly Asn Ser Xaa Tyr Phe Phe His Pro
                85                  90                  95

Asp Asn Gln Xaa Asp Ala Glu Ala Ile Thr His Leu Phe Thr Asp Xaa
            100                 105                 110

Gln Asn Arg Tyr Thr Phe Ala Phe Gly Gly Asn Tyr Asp Arg Leu Glu
        115                 120                 125

Gln Leu Ala Gly Asn Leu Arg Glu Asn Ile Glu Leu Gly Asn Gly Pro
130                 135                 140

Leu Glu Glu Ala Ile Ser Ala Leu Tyr Tyr Tyr Ser Thr Gly Gly Thr
145                 150                 155                 160

Gln Leu Pro Thr Leu Ala Arg Ser Phe Ile Ile Cys Ile Gln Met Ile
                165                 170                 175

Ser Glu Ala Ala Arg Phe Gln Tyr Ile Glu Gly Glu Met Arg Thr Arg
            180                 185                 190

Ile Arg Tyr Asn Arg Arg Ser
            195

<210> SEQ ID NO 17
<211> LENGTH: 189
<212> TYPE: PRT
<213> ORGANISM: Artificial Sequence
<220> FEATURE:
<223> OTHER INFORMATION: (SS)RTA based on Ricinus communis
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (65)..(68)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 17

Met Ile Phe Pro Lys Gln Tyr Pro Ile Ile Asn Phe Thr Thr Ala Gly
1               5                   10                  15

Ala Thr Val Gln Ser Tyr Thr Asn Phe Ile Arg Ala Val Arg Gly Arg
            20                  25                  30

Leu Thr Val Leu Pro Asn Xaa Xaa Gly Leu Pro Ile Asn Gln Arg Phe
        35                  40                  45

Ile Leu Val Glu Leu Ser Asn His Ala Glu Leu Ser Val Thr Leu Ala
    50                  55                  60
```

```
Xaa Xaa Xaa Xaa Asn Ala Tyr Val Val Gly Tyr Arg Ala Gly Asn Ser
 65                  70                  75                  80

Xaa Tyr Phe Phe His Pro Asp Asn Gln Xaa Asp Ala Glu Ala Ile Thr
                 85                  90                  95

His Leu Phe Thr Asp Xaa Gln Asn Arg Tyr Thr Phe Ala Phe Gly Gly
            100                 105                 110

Asn Tyr Asp Arg Leu Glu Gln Leu Ala Gly Asn Leu Arg Glu Asn Ile
        115                 120                 125

Glu Leu Gly Asn Gly Pro Leu Glu Glu Ala Ile Ser Ala Leu Tyr Tyr
    130                 135                 140

Tyr Ser Thr Gly Gly Thr Gln Leu Pro Thr Leu Ala Arg Ser Phe Ile
145                 150                 155                 160

Ile Cys Ile Gln Met Ile Ser Glu Ala Ala Arg Phe Gln Tyr Ile Glu
                165                 170                 175

Gly Glu Met Arg Thr Arg Ile Arg Tyr Asn Arg Arg Ser
            180                 185

<210> SEQ ID NO 18
<211> LENGTH: 198
<212> TYPE: PRT
<213> ORGANISM: Artificial Sequence
<220> FEATURE:
<223> OTHER INFORMATION: (SS)RTA based on Ricinus communis
<220> FEATURE:
<221> NAME/KEY: misc_feature
<222> LOCATION: (48)..(49)
<223> OTHER INFORMATION: Xaa can be any naturally occurring amino acid
<220> FEATURE:
<221> NAME/KEY: misc_feature
<222> LOCATION: (74)..(77)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid

<400> SEQUENCE: 18

Met Val Pro Lys Gln Tyr Pro Ile Ile Asn Phe Thr Thr Ala Gly Ala
  1               5                  10                  15

Thr Val Gln Ser Tyr Thr Asn Phe Ile Arg Ala Val Arg Gly Arg Leu
                20                  25                  30

Thr Thr Gly Ala Asp Val Arg His Glu Ile Pro Val Leu Pro Asn Xaa
             35                  40                  45

Xaa Gly Leu Pro Ile Asn Gln Arg Phe Ile Leu Val Glu Leu Ser Asn
 50                  55                  60

His Ala Glu Leu Ser Val Thr Leu Ala Xaa Xaa Xaa Asn Ala Tyr
 65                  70                  75                  80

Val Val Gly Tyr Arg Ala Gly Asn Ser Xaa Tyr Phe His Pro Asp
                 85                  90                  95

Asn Gln Xaa Asp Ala Glu Ala Ile Thr His Leu Phe Thr Asp Xaa Gln
            100                 105                 110

Asn Arg Tyr Thr Phe Ala Phe Gly Gly Asn Tyr Asp Arg Leu Glu Gln
        115                 120                 125

Leu Ala Gly Asn Leu Arg Glu Asn Ile Glu Leu Gly Asn Gly Pro Leu
```

```
            130                 135                 140
Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
                165                 170                 175

Glu Ala Ala Arg Phe Gln Tyr Ile Glu Gly Glu Met Arg Thr Arg Ile
            180                 185                 190

Arg Tyr Asn Arg Arg Ser
        195

<210> SEQ ID NO 19
<211> LENGTH: 188
<212> TYPE: PRT
<213> ORGANISM: Artificial Sequence
<220> FEATURE:
<223> OTHER INFORMATION: (SS)RTA based on Ricinus communis
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (64)..(67)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 19

Met Val Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Val Leu Pro Asn Xaa Xaa Gly Leu Pro Ile Asn Gln Arg Phe Ile
        35                  40                  45

Leu Val Glu Leu Ser Asn His Ala Glu Leu Ser Val Thr Leu Ala Xaa
    50                  55                  60

Xaa Xaa Xaa Asn Ala Tyr Val Val Gly Tyr Arg Ala Gly Asn Ser Xaa
65                  70                  75                  80

Tyr Phe Phe His Pro Asp Asn Gln Xaa Asp Ala Glu Ala Ile Thr His
                85                  90                  95

Leu Phe Thr Asp Xaa Gln Asn Arg Tyr Thr Phe Ala Phe Gly Gly Asn
            100                 105                 110

Tyr Asp Arg Leu Glu Gln Leu Ala Gly Asn Leu Arg Glu Asn Ile Glu
        115                 120                 125

Leu Gly Asn Gly Pro Leu Glu Glu Ala Ile Ser Ala Leu Tyr Tyr Tyr
    130                 135                 140

Ser Thr Gly Gly Thr Gln Leu Pro Thr Leu Ala Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Ile Arg Tyr Asn Arg Arg Ser
            180                 185
```

<210> SEQ ID NO 20
<211> LENGTH: 185
<212> TYPE: PRT
<213> ORGANISM: Artificial Sequence
<220> FEATURE:
<223> OTHER INFORMATION: (SS)RTA based on Ricinus communis
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (61)..(64)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid

<400> SEQUENCE: 20

```
Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Asn Xaa Xaa Gly Leu Pro Ile Asn Gln Arg Phe Ile Leu Val Glu
        35                  40                  45

Leu Ser Asn His Ala Glu Leu Ser Val Thr Leu Ala Xaa Xaa Xaa Xaa
50                  55                  60

Asn Ala Tyr Val Val Gly Tyr Arg Ala Gly Asn Ser Xaa Tyr Phe Phe
65                  70                  75                  80

His Pro Asp Asn Gln Xaa Asp Ala Glu Ala Ile Thr His Leu Phe Thr
                85                  90                  95

Asp Xaa Gln Asn Arg Tyr Thr Phe Ala Phe Gly Gly Asn Tyr Asp Arg
            100                 105                 110

Leu Glu Gln Leu Ala Gly Asn Leu Arg Glu Asn Ile Glu Leu Gly Asn
        115                 120                 125

Gly Pro Leu Glu Glu Ala Ile Ser Ala Leu Tyr Tyr Tyr Ser Thr Gly
    130                 135                 140

Gly Thr Gln Leu Pro Thr Leu Ala Arg Ser Phe Ile Ile Cys Ile Gln
145                 150                 155                 160

Met Ile Ser Glu Ala Ala Arg Phe Gln Tyr Ile Glu Gly Glu Met Arg
                165                 170                 175

Thr Arg Ile Arg Tyr Asn Arg Arg Ser
            180                 185
```

<210> SEQ ID NO 21
<211> LENGTH: 200
<212> TYPE: PRT
<213> ORGANISM: Artificial Sequence
<220> FEATURE:
<223> OTHER INFORMATION: (SS)RTA based on Ricinus communis
<220> FEATURE:
<221> NAME/KEY: misc_feature
<222> LOCATION: (49)..(50)
<223> OTHER INFORMATION: Xaa can be any naturally occurring amino acid
<220> FEATURE:

<221> NAME/KEY: misc_feature
<222> LOCATION: (75)..(78)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid

<400> SEQUENCE: 21

Met Ile Phe Pro Lys Gln Tyr Pro Ile Asn Phe Thr Thr Ala Gly
 1               5                  10                  15

Ala Thr Val Gln Ser Tyr Thr Asn Phe Ile Arg Ala Val Arg Gly Arg
             20                  25                  30

Leu Thr Thr Gly Ala Asp Val Arg His Glu Ile Pro Val Leu Pro Asn
         35                  40                  45

Xaa Xaa Gly Leu Pro Ile Asn Gln Arg Phe Ile Leu Val Glu Leu Ser
 50                  55                  60

Asn His Ala Glu Leu Ser Val Thr Leu Ala Xaa Xaa Xaa Xaa Asn Ala
65                  70                  75                  80

Tyr Val Val Gly Tyr Arg Ala Gly Asn Ser Xaa Tyr Phe Phe His Pro
                 85                  90                  95

Asp Asn Gln Xaa Asp Ala Glu Ala Ile Thr His Leu Phe Thr Asp Xaa
            100                 105                 110

Gln Asn Arg Tyr Thr Phe Ala Phe Gly Gly Asn Tyr Asp Arg Leu Glu
        115                 120                 125

Gln Leu Ala Gly Asn Leu Arg Glu Asn Ile Glu Leu Gly Asn Gly Pro
    130                 135                 140

Leu Glu Glu Ala Ile Ser Ala Leu Tyr Tyr Tyr Ser Thr Gly Gly Thr
145                 150                 155                 160

Gln Leu Pro Thr Leu Ala Arg Ser Phe Ile Ile Cys Ile Gln Met Ile
                165                 170                 175

Ser Glu Ala Ala Arg Phe Gln Tyr Ile Glu Gly Glu Met Arg Thr Arg
            180                 185                 190

Ile Arg Tyr Asn Arg Arg Ser Ala
        195                 200

<210> SEQ ID NO 22
<211> LENGTH: 190
<212> TYPE: PRT
<213> ORGANISM: Artificial Sequence
<220> FEATURE:
<223> OTHER INFORMATION: (SS)RTA based on Ricinus communis
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (65)..(68)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (90)..(90)

```
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 22

Met Ile Phe Pro Lys Gln Tyr Pro Ile Ile Asn Phe Thr Thr Ala Gly
1               5                   10                  15

Ala Thr Val Gln Ser Tyr Thr Asn Phe Ile Arg Ala Val Arg Gly Arg
            20                  25                  30

Leu Thr Val Leu Pro Asn Xaa Xaa Gly Leu Pro Ile Asn Gln Arg Phe
        35                  40                  45

Ile Leu Val Glu Leu Ser Asn His Ala Glu Leu Ser Val Thr Leu Ala
50                  55                  60

Xaa Xaa Xaa Xaa Asn Ala Tyr Val Val Gly Tyr Arg Ala Gly Asn Ser
65                  70                  75                  80

Xaa Tyr Phe Phe His Pro Asp Asn Gln Xaa Asp Ala Glu Ala Ile Thr
                85                  90                  95

His Leu Phe Thr Asp Xaa Gln Asn Arg Tyr Thr Phe Ala Phe Gly Gly
            100                 105                 110

Asn Tyr Asp Arg Leu Glu Gln Leu Ala Gly Asn Leu Arg Glu Asn Ile
        115                 120                 125

Glu Leu Gly Asn Gly Pro Leu Glu Glu Ala Ile Ser Ala Leu Tyr Tyr
130                 135                 140

Tyr Ser Thr Gly Gly Thr Gln Leu Pro Thr Leu Ala Arg Ser Phe Ile
145                 150                 155                 160

Ile Cys Ile Gln Met Ile Ser Glu Ala Ala Arg Phe Gln Tyr Ile Glu
                165                 170                 175

Gly Glu Met Arg Thr Arg Ile Arg Tyr Asn Arg Arg Ser Ala
            180                 185                 190

<210> SEQ ID NO 23
<211> LENGTH: 188
<212> TYPE: PRT
<213> ORGANISM: Artificial Sequence
<220> FEATURE:
<223> OTHER INFORMATION: Unsuitable (SS)RTA N141C/I192C based on Ricinus
      communis

<400> SEQUENCE: 23

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Val Leu Pro Asn Arg Val Gly Leu Pro Ile Asn Gln Arg Phe Ile
        35                  40                  45

Leu Val Glu Leu Ser Asn His Ala Glu Leu Ser Val Thr Leu Ala Leu
50                  55                  60

Asp Val Thr Asn Ala Tyr Val Val Gly Tyr Arg Ala Gly Asn Ser Ala
65                  70                  75                  80

Tyr Phe Phe His Pro Asp Asn Gln Glu Asp Ala Glu Ala Ile Thr His
                85                  90                  95

Leu Phe Thr Asp Val Gln Asn Arg Tyr Thr Phe Ala Phe Gly Gly Asn
            100                 105                 110

Tyr Asp Arg Leu Glu Gln Leu Ala Gly Asn Leu Arg Glu Asn Ile Glu
        115                 120                 125
```

```
Leu Gly Cys Gly Pro Leu Glu Glu Ala Ile Ser Ala Leu Tyr Tyr Tyr
130                 135                 140

Ser Thr Gly Gly Thr Gln Leu Pro Thr Leu Ala Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Cys Arg Tyr Asn Arg Ser
            180                 185
```

<210> SEQ ID NO 24
<211> LENGTH: 188
<212> TYPE: PRT
<213> ORGANISM: Artificial Sequence
<220> FEATURE:
<223> OTHER INFORMATION: Unsuitable (SS)RTA R125C/A165C based on Ricinus communis

<400> SEQUENCE: 24

```
Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
                20                  25                  30

Thr Val Leu Pro Asn Arg Val Gly Leu Pro Ile Asn Gln Arg Phe Ile
            35                  40                  45

Leu Val Glu Leu Ser Asn His Ala Glu Leu Ser Val Thr Leu Ala Leu
50                  55                  60

Asp Val Thr Asn Ala Tyr Val Val Gly Tyr Arg Ala Gly Asn Ser Ala
65                  70                  75                  80

Tyr Phe Phe His Pro Asp Asn Gln Glu Asp Ala Glu Ala Ile Thr His
                85                  90                  95

Leu Phe Thr Asp Val Gln Asn Arg Tyr Thr Phe Ala Phe Gly Gly Asn
            100                 105                 110

Tyr Asp Cys Leu Glu Gln Leu Ala Gly Asn Leu Arg Glu Asn Ile Glu
        115                 120                 125

Leu Gly Asn Gly Pro Leu Glu Glu Ala Ile Ser Ala Leu Tyr Tyr Tyr
130                 135                 140

Ser Thr Gly Gly Thr Gln Leu Pro Thr Leu Cys Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Ile Arg Tyr Asn Arg Ser
            180                 185
```

<210> SEQ ID NO 25
<211> LENGTH: 188
<212> TYPE: PRT
<213> ORGANISM: Artificial Sequence
<220> FEATURE:
<223> OTHER INFORMATION: Unsuitable (SS)RTA R48C/T77C/V76I based on Ricinus communis

<400> SEQUENCE: 25

```
Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
                20                  25                  30

Thr Val Leu Pro Asn Cys Val Gly Leu Pro Ile Asn Gln Arg Phe Ile
            35                  40                  45
```

```
Leu Val Glu Leu Ser Asn His Ala Glu Leu Ser Val Thr Leu Ala Leu
 50                  55                  60

Asp Ile Cys Asn Ala Tyr Val Val Gly Tyr Arg Ala Gly Asn Ser Ala
 65                  70                  75                  80

Tyr Phe Phe His Pro Asp Asn Gln Glu Asp Ala Glu Ala Ile Thr His
                 85                  90                  95

Leu Phe Thr Asp Val Gln Asn Arg Tyr Thr Phe Ala Phe Gly Gly Asn
                100                 105                 110

Tyr Asp Arg Leu Glu Gln Leu Ala Gly Asn Leu Arg Glu Asn Ile Glu
            115                 120                 125

Leu Gly Asn Gly Pro Leu Glu Glu Ala Ile Ser Ala Leu Tyr Tyr Tyr
130                 135                 140

Ser Thr Gly Gly Thr Gln Leu Pro Thr Leu Ala Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Ile Arg Tyr Asn Arg Arg Ser
            180                 185
```

<210> SEQ ID NO 26
<211> LENGTH: 188
<212> TYPE: PRT
<213> ORGANISM: Artificial Sequence
<220> FEATURE:
<223> OTHER INFORMATION: Unsuitable (SS)RTA E138C/P143C based on Ricinus communis

<400> SEQUENCE: 26

```
Ile Phe Pro Lys Gln Tyr Pro Ile Ile Asn Phe Thr Thr Ala Gly Ala
 1               5                  10                  15

Thr Val Gln Ser Tyr Thr Asn Phe Ile Arg Ala Val Arg Gly Arg Leu
                20                  25                  30

Thr Val Leu Pro Asn Arg Val Gly Leu Pro Ile Asn Gln Arg Phe Ile
             35                  40                  45

Leu Val Glu Leu Ser Asn His Ala Glu Leu Ser Val Thr Leu Ala Leu
 50                  55                  60

Asp Val Thr Asn Ala Tyr Val Val Gly Tyr Arg Ala Gly Asn Ser Ala
 65                  70                  75                  80

Tyr Phe Phe His Pro Asp Asn Gln Glu Asp Ala Glu Ala Ile Thr His
                 85                  90                  95

Leu Phe Thr Asp Val Gln Asn Arg Tyr Thr Phe Ala Phe Gly Gly Asn
                100                 105                 110

Tyr Asp Arg Leu Glu Gln Leu Ala Gly Asn Leu Arg Glu Asn Ile Cys
            115                 120                 125

Leu Gly Asn Gly Cys Leu Glu Glu Ala Ile Ser Ala Leu Tyr Tyr Tyr
130                 135                 140

Ser Thr Gly Gly Thr Gln Leu Pro Thr Leu Ala Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Ile Arg Tyr Asn Arg Arg Ser
            180                 185
```

<210> SEQ ID NO 27
<211> LENGTH: 188

<212> TYPE: PRT
<213> ORGANISM: Artificial Sequence
<220> FEATURE:
<223> OTHER INFORMATION: Unsuitable (SS)RTA Q128C/A165C based on Ricinus
      communis

<400> SEQUENCE: 27

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Val Leu Pro Asn Arg Val Gly Leu Pro Ile Asn Gln Arg Phe Ile
        35                  40                  45

Leu Val Glu Leu Ser Asn His Ala Glu Leu Ser Val Thr Leu Ala Leu
    50                  55                  60

Asp Val Thr Asn Ala Tyr Val Val Gly Tyr Arg Ala Gly Asn Ser Ala
65                  70                  75                  80

Tyr Phe Phe His Pro Asp Asn Gln Glu Asp Ala Glu Ala Ile Thr His
                85                  90                  95

Leu Phe Thr Asp Val Gln Asn Arg Tyr Thr Phe Ala Phe Gly Gly Asn
            100                 105                 110

Tyr Asp Arg Leu Glu Cys Leu Ala Gly Asn Leu Arg Glu Asn Ile Glu
        115                 120                 125

Leu Gly Asn Gly Pro Leu Glu Glu Ala Ile Ser Ala Leu Tyr Tyr Tyr
    130                 135                 140

Ser Thr Gly Gly Thr Gln Leu Pro Thr Leu Cys Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Ile Arg Tyr Asn Arg Arg Ser
            180                 185

<210> SEQ ID NO 28
<211> LENGTH: 570
<212> TYPE: DNA
<213> ORGANISM: Artificial Sequence
<220> FEATURE:
<223> OTHER INFORMATION: Codon-optimized sequence for RTA1-33/44-198
      based on Ricinus communis

<400> SEQUENCE: 28
atgatcttcc cgaaacagta cccgatcatc aacttcacca ccgcaggtgc aaccgttcag      60
tcttacacca acttcatccg tgcagttcgt ggtcgcctga ccgttctgcc gaaccgtgtt     120
ggtctgccga tcaaccagcg tttcatcctg gtagaactgt ctaaccacgc agaactgtct     180
gttaccctgg cactggacgt taccaacgcg tacgtagtgg gctaccgtgc gggtaactct     240
gcatacttct tccacccaga caaccaggag gacgcagaag caatcaccca cctgttcacc     300
gacgttcaga accgttacac cttcgcgttc ggtggcaact acgatcgtct ggaacagctg     360
gcaggtaacc tgcgtgagaa catcgaactg ggtaacggtc cgctggaaga ggcgatctct     420
gcgctgtact actattctac cggtggtacc cagctgccga ccctggcgcg ttctttcatc     480
atctgcatcc agatgatctc tgaagcggca cgtttccagt acatcgaagg tgaaatgcgt     540
acccgtatcc gttacaaccg tcgttcttag                                     570

RICIN VACCINE AND METHODS OF MAKING THEREOF

CROSS REFERENCE TO RELATED APPLICATIONS

This application is a 371 National Phase entry of PCT/US2011/033486, filed 21 Apr. 2011, and claims the benefit of U.S. Patent Application No. 61/343,944, filed 22 Apr. 2010, all of which are herein incorporated by reference in their entirety.

ACKNOWLEDGMENT OF GOVERNMENT SUPPORT

This invention was made by employees of the United States Army. The government has certain rights in this invention.

REFERENCE TO A SEQUENCE LISTING SUBMITTED VIA EFS-WEB

The content of the ASCII text file of the sequence listing named "20110421_034047_056WO1_ST25" which is 41.9 KB in size was created on 21 Apr. 2011 and electronically submitted via EFS-Web herewith the application is incorporated herein by reference in its entirety.

BACKGROUND OF THE INVENTION

1. Field of the Invention

The present invention generally relates to ricin vaccines and methods of making and using thereof.

2. Description of the Related Art

Ricin is a very toxic protein obtained from the castor bean, *Ricinus communis*, Euphorbiaceae. Ricin is a heterodimer comprising an A chain and a B chain joined by a disulfide bond. Ricin A chain (RTA) is an N-glycosidase enzyme that irreversibly damages (i.e. hydrolyzes) a specific adenine base from 28S rRNA. Once the rRNA has been damaged, the cell cannot make protein and will inevitably die (cytotoxicity). As RTA exhibits this type of destructive catalytic activity, RTA is commonly referred to as a type II ribosome inactivating protein (RIP). See Lord, et al. (1991) Semin. Cell Biol. 2(1):15-22. RTA has been coupled with a targeting moiety to selectively destroy target cells such as tumor cells. See U.S. Pat. Nos. 4,80,457; 4,962,188; and 4,689,401; see also Vitetta et al. (1993) Trends Pharmacol. Sci. 14:148-154 and Ghetie & Vitetta (1994) Cancer Drug Delivery 2:191-198.

The toxic consequences of ricin are due to the biological activity of RTA. Ricin B chain (RTB) binds the toxin to cell surface receptors and then RTA is transferred inside the cell where inhibition of ribosome activity occurs. The human lethal dose of ricin toxin is about 1 µg/kg. As highly purified ricin is commercially available, the use of ricin toxin in biological warfare and terrorism is highly possible and probable. Unfortunately, there is no effective antidote for toxic exposure to ricin. Thus, attempts have been made to provide vaccines against ricin intoxication.

Ricin vaccines have been prepared by isolating the natural toxin from castor beans, and treating the toxin with harsh chemicals, typically formaldehyde, to reduce the toxic activity. See Hewetson, et al. (1993) Vaccine 11(7):743-746; Griffiths, et al. (1995) Hum. Exp. Toxicol. 14(2):155-164; Griffiths, et al. (1999) Vaccine 17(20-21):2562-2568; and Yan, et al. (1996) Vaccine 14(11):1031-1038. The first generation vaccines are called "toxoid" vaccines as they are made directly from natural toxin itself. The second generation ricin vaccines comprise wild-type (wt) RTA, but not RTB. The second generation ricin vaccines include deglycosylated RTA (dgRTA) vaccines. The third generation ricin vaccines contain amino acid substitutions in the active site of RTA which result in reduced N-glycosidase activity (e.g Y80A mutations) and/or reduced Vascular Leak Syndrome (VLS) (e.g. Y76M mutations). The fourth generation ricin vaccines contain amino acid deletions and truncations in the RTA which increase the stability of the RTA molecule. See, for example, U.S. Pat. No. 6,869,787.

Since RTA vaccines are limited by their propensity to self-aggregate and denature at or near production and storage temperatures (35-40° C.), a need still exists for ricin vaccines that have a reduced ability to self-aggregate and are thermally stable under production and storage conditions, yet remain therapeutically effective.

SUMMARY OF THE INVENTION

The present invention generally relates to polypeptides related to ricin toxin A chain.

In some embodiments, the present invention provides an isolated polypeptide comprising, consisting essentially of, or consisting of an amino acid molecule which contains a first sequence that has at least 80, 81, 82, 83, 84, 85, 86, 87, 88, 89, 90, 91, 92, 93, 94, 95, 96, 97, 98, 99, or 100% sequence identity to

```
                                          (SEQ ID NO: 4)
X1X2GLPINQRFILVELSNHAELSVILAX4X5X6X1NAYVVGYRAGNSX3YFFHPDNQX2DAEAI

THLFTDX3
``` wherein both X1's are C, both X2's are C, or both X3's are C,
X4 is L, F, C, M, A, T, S, W, Y, P, H, E, Q, D, N, K, or R,
X5 is D, I, V, L, F, C, M, A, G, T, S, W, Y, P, H, E, Q, N, K, or R,
X6 is V, I, F, C, M, A, G, T, W, Y, P, H, E, Q, D, N, K, or R, and
wherein when both X1's are C, X6 is not I. In some embodiments, when both X1's are C, X5 is D or N and X6 is V, when both X2's are C, X5 is D and X6 is V or I or X5 is N and X6 is V, and when both X3's are C, X5 is D and X6 is V. In some embodiments, the amino acid molecule contains a second sequence that has at least 80, 81, 82, 83, 84, 85, 86, 87, 88, 89, 90, 91, 92, 93, 94, 95, 96, 97, 98, 99, or 100% sequence identity to

```
                                          (SEQ ID NO: 5)
MIFPKQYPIINFTTAGATVQSYTNFIRAVRGRLTTGADVRHEIPVLPN, (SEQ ID NO: 6)
IFPKQYPIINFTTAGATVQSYTNFIRAVRGRLTTGADVRHEIPVLPN, (SEQ ID NO: 7)
MVPKQYPIINFTTAGATVQSYTNFIRAVRGRLTTGADVRHEIPVLPN, (SEQ ID NO: 8)
MIFPKQYPIINFTTAGATVQSYTNFIRAVRGRLTVLPN,
```

```
                                                    (SEQ ID NO: 9)
MVPKQYPIINFTTAGATVQSYTNFIRAVRGRLTVLPN, (SEQ ID NO: 10)
IFPKQYPIINFTTAGATVQSYTNFIRAVRGRLTVLPN,
or
                                                    (SEQ ID NO: 11)
IFPKQYPIINFTTAGATVQSYTNFIRAVRGRLTN
``` and/or a third sequence that has at least 80, 81, 82, 83, 84, 85, 86, 87, 88, 89, 90, 91, 92, 93, 94, 95, 96, 97, 98, 99, or 100% sequence identity to

```
                                                    (SEQ ID NO: 12)
QNRYTFAFGGNYDRLEQLAGNLRENIELGNGPLEEAISALYYYSTGGTQLPTLARSFIICIQMI

SEAARFQYIEGEMRTRIRYNRRS,
or
                                                    (SEQ ID NO: 13)
QNRYTFAFGGNYDRLEQLAGNLRENIELGNGPLEEAISALYYYSTGGTQLPTLARSFIICIQMIS

EAARFQYIEGEMRTRIRYNRRSA.
```

In some embodiments, the second sequence is conjugated to the N-terminus of the first sequence and/or the third sequence is conjugated to the C-terminus of the first sequence.

In some embodiments, the present invention provides an isolated polypeptide comprising, consisting essentially of, or consisting of an amino acid molecule which contains a first sequence that has at least 80, 81, 82, 83, 84, 85, 86, 87, 88, 89, 90, 91, 92, 93, 94, 95, 96, 97, 98, 99, or 100% sequence identity to

```
(SS)RTA 198:
                                                    (SEQ ID NO: 14)
IFPKQYPIINFTTAGATVQSYTNFIRAVRGRLTTGADVRHEIPVLPNX1X2GLPINQRFILVELS

NHAELSVTLAX4X5X6X1NAYVVGYRAGNSX3YFFHPDNQX2DAEAITHLFTDX3QNRYTFAFGG

NYDRLEQLAGNLRENIELGNGPLEEAISALYYYSTGGTQLPTLARSFIICIQMISEAARFQYIEG

EMRTRIRYNRRS;
or (SS)RTA 1-33/44-198:
                                                    (SEQ ID NO: 15)
IFPKQYPIINFTTAGATVQSYTNFIRAVRGRLTVLPNX1X2GLPINQRFILVELSNHAELSVTLA

X4X5X6X1NAYVVGYRAGNSX3YFFHPDNQX2DAEAITHLFTDX3QNRYTFAFGGNYDRLEQLAG

NLRENIELGNGPLEEAISALYYYSTGGTQLPTLARSFIICIQMISEAARFQYIEGEMRTRIRYNR

RS
``` wherein both X1's are C, both X2's are C, or both X3's are C,
X4 is L, F, C, M, A, T, S, W, Y, P, H, E, Q, D, N, K, or R,
X5 is D, I, V, L, F, C, M, A, G, T, S, W, Y, P, H, E, Q, N, K, or R,
X6 is V, I, F, C, M, A, G, T, W, Y, P, H, E, Q, D, N, K, or R, and wherein when both X1's are C, X6 is not I. In some embodiments, when both X1's are C, X5 is D or N and X6 is V, when both X2's are C, X5 is D and X6 is V or I or X5 is N and X6 is V, and when both X3's are C, X5 is D and X6 is V.

In some embodiments, the (SS)RTA polypeptides according to the instant invention retain the functional integrity of the neutralizing immunological epitope of wild type ricin A chain (SEQ ID NO:1), RTA 198 (SEQ ID NO:2), and/or RTA 1-33/44-198 (SEQ ID NO:3).

In some embodiments, the (SS)RTA polypeptides according to the instant invention have an aqueous solubility that is greater than the solubility of wild type ricin A chain (SEQ ID NO:1), RTA 198 (SEQ ID NO:2), and/or RTA 1-33/44-198 (SEQ ID NO:3).

In some embodiments, the present invention provides polynucleotides that encode the (SS)RTA polypeptides of the instant invention. In some embodiments, the polynucleotide is codon-optimized using methods known in the art.

In some embodiments, the present invention provides antibodies raised against the (SS)RTA polypeptides of the instant invention. In some embodiments, an antibody according to the instant invention is a neutralizing antibody that is capable of neutralizing ricin, ricin A chain, or both.

In some embodiments, the present invention provides pharmaceutical compositions which comprise, consist essentially of, or consists of at least one (SS)RTA polypeptide according to the instant invention and/or at least one antibody raised against at least one (SS)RTA polypeptide according to the instant invention and a pharmaceutically acceptable vehicle, and optionally an adjuvant. The pharmaceutical composition may be capable of eliciting an immune response when administered to a subject. The immune response may be a protective immune response against ricin intoxication. In some embodiments, the composition is a vaccine which comprises an immunogenic amount of at least one at least one (SS)RTA polypeptide according to the instant invention.

In some embodiments, the present invention provides a method of inducing an immune response in a subject which comprises administering to the subject at least one immunogenic amount of at least one (SS)RTA of the present invention. Preferably, the subject is mammalian, more preferably, the subject is human. The method may further comprise administering to the subject at least one booster dose.

In some embodiments, the present invention provides a method of providing passive immunity against ricin intoxication in a subject comprising administering to the subject a therapeutically effective amount of at least one antibody raised against at least one (SS)RTA of the present invention.

In some embodiments, the present invention provides a method of treating, inhibiting, reducing, or preventing ricin intoxication in a subject comprising administering to the subject a therapeutically effective amount of at least one (SS) RTA of the present invention, a therapeutically effective amount of at least one antibody raised against a (SS)RTA of the present invention, and/or a composition thereof.

In some embodiments the present invention provides a kit comprising at least one (SS)RTA of the present invention, at least one antibody raised against a (SS)RTA of the present invention, at least one polynucleotide which encodes a (SS) RTA of the present invention and/or a composition thereof packaged together with instructions for use. The kits may further comprise diagnostic reagents such as labeling compounds for detecting the presence of ricin toxin or for diagnosing exposure of a subject to ricin. The kits may comprise drug delivery devices for administering the compositions of the present invention to a subject.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

DETAILED DESCRIPTION OF THE INVENTION

Figure 1:
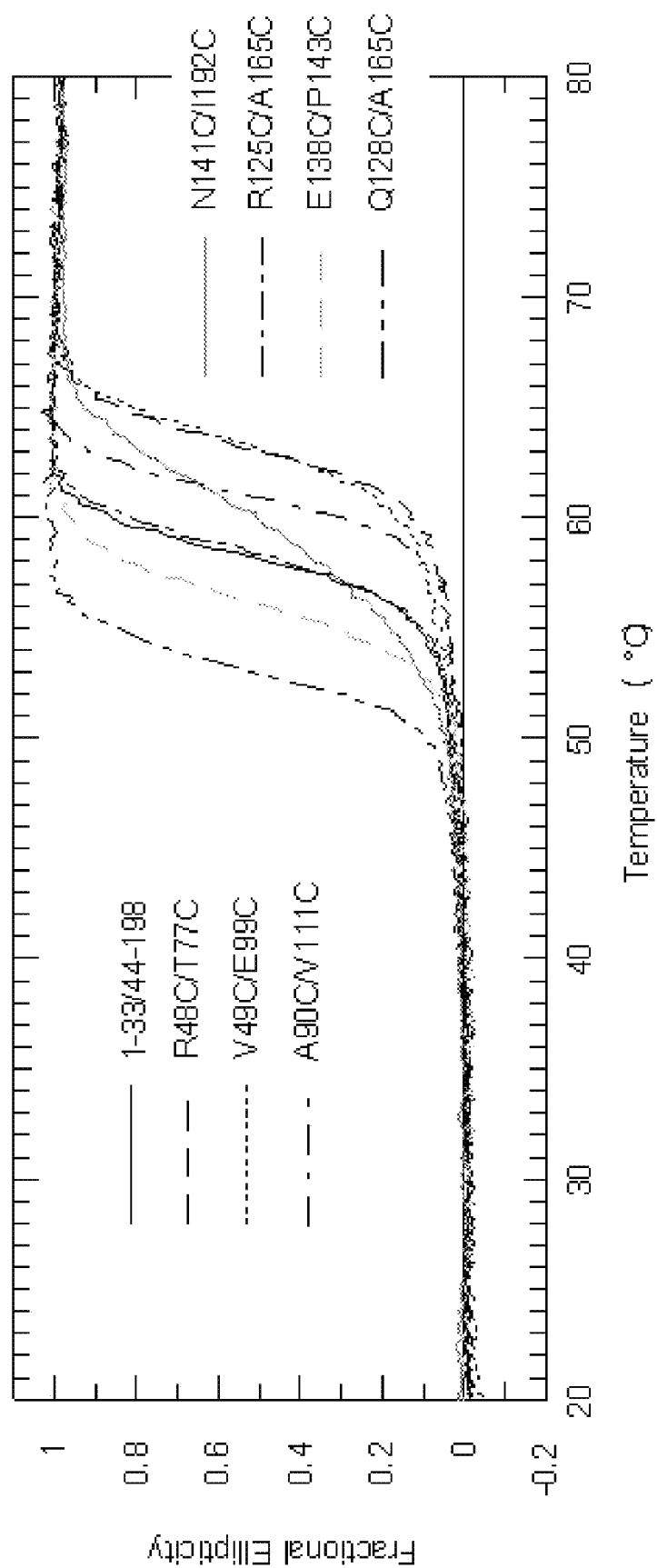
FIG. 1 shows the melting temperatures of various (SS)RTA 1-33/44-198 variants, i.e. RTA 1-33/44-198, RTA 1-33/44-198 R48C/T77C, RTA 1-33/44-198 V49C/E89C, RTA 1-33/44-198 A90C/E99C, RTA 1-33/44-198 N141C/I92C, RTA 1-33/44-198 R125C/A165C, RTA 1-33/44-198 E138C/P143, RTA 1-33/44-198 Q128C/A165C. Thermal denaturation of each variant was monitored by circular dichroism at 222 nm from 10-80° C. RTA 1-33/44-198 R48C/T77C and RTA 1-33/44-198 V49C/E99C were found to have higher melting temperatures (by 5° C.) than the RTA 1-33/44-198 at pH 7.4.
Figure 2:
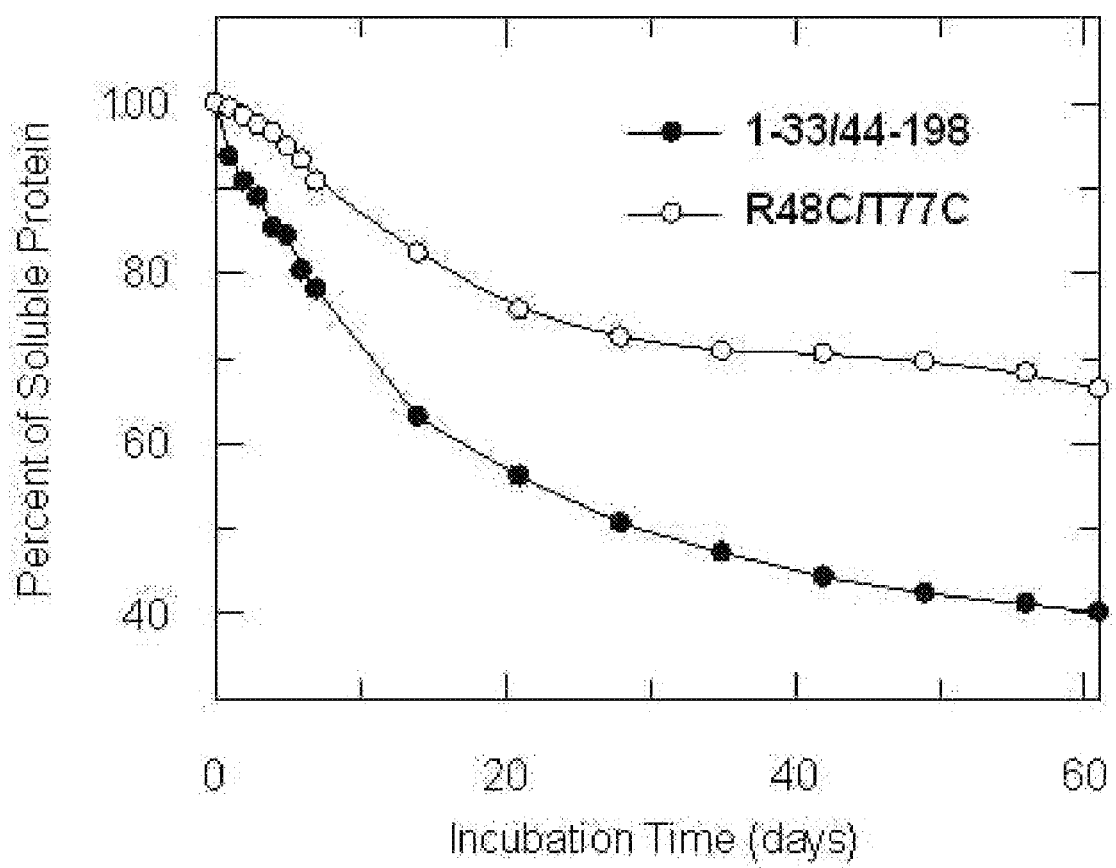
FIG. 2 shows the solution storage time for RTA1-33/44-198 and RTA1-33/44-198 R48C/T77C. Solutions of each highly purified (>90% purity by PAGE) recombinant immunogen were prepared in PBS pH 7.4 and stored at a fixed starting concentration (0.2-, 1.0-, or 2.0-mg/mL) in a sealed tube at 37° C. At various time points, tubes were removed from incubation and centrifuged (14,000 rpm for 5 min) to pellet insoluble protein aggregates. The amount of protein remaining in solution was measured by absorbance at 280 nm, and expressed as % of the starting protein concentration. For each time point, three separate tubes were sampled and % calculated, and then the average %+SE was tabulated. 40% of the parent RTA 1-33/44-198 molecule (dot) remained soluble after 61 days at 37° C. (phosphate buffered saline, pH 7.4. 1 mg/mL), whereas 66% of the RTA 1-33/44-198 R48C/T77C variant (diamond) remained soluble after 61 days under identical conditions (Table 2).

The present invention provides polypeptides derived from wild type ricin. The complete ricin sequence is Accession Number PO2879.1 which is herein incorporated by reference. In particular, the present invention provides polypeptides derived from wild type ricin A chain (wt RTA):

(SEQ ID NO: 1)
IFPKQYPIINFTTAGATVQSYTNFIRAVRGRLTTGADVRHEIPVLPNRVGLPINQRFILVELSNH

AELSVTLALDVTNAYVVGYRAGNSAYFFHPDNQEDAEAITHLFTDVQNRYTFAFGGNYDRLEQLA

GNLRENIELGNGPLEEAISALYYYSTGGTQLPTLARSFIICIQMISEAARFQYIEGEMRTRIRYNRRSAPD

PSVITLENSWGRLSTAIQESNQGAFASPIQLQRRNGSKFSVYDVSILIPIIALMVYRCAPPPSSQF,

RTA 198:

(SEQ ID NO: 2)
IFPKQYPIINFTTAGATVQSYTNFIRAVRGRLTTGADVRHEIPVLPNRVGLPINQRFILVELSNH

AELSVTLALDVTNAYVVGYRAGNSAYFFHPDNQEDAEAITHLFTDVQNRYTFAFGGNYDRLEQLA

GNLRENIELGNGPLEEAISALYYYSTGGTQLPTLARSFIICIQMISEAARFQYIEGEMRTRIRYN

RRS,
and/or

RTA 1-33/44-198:

(SEQ ID NO: 3)
IFPKQYPIINFTTAGATVQSYTNFIRAVRGRLTVLPNRVGLPINQRFILVELSNHAELSVTLALD

VTNAYVVGYRAGNSAYFFHPDNQEDAEAITHLFTDVQNRYTFAFGGNYDRLEQLAGNLRENIELG

NGPLEEAISALYYYSTGGTQLPTLARSFIICIQMISEAARFQYIEGEMRTRIRYNRRS for use in compositions and methods for treating, inhibiting or preventing ricin intoxication in a subject.

In particular, the present invention provides an isolated polypeptide comprising, consisting essentially of, or consisting of an amino acid molecule which contains a first sequence that has at least 80, 81, 82, 83, 84, 85, 86, 87, 88, 89, 90, 91, 92, 93, 94, 95, 96, 97, 98, 99, or 100% sequence identity to

```
                                                    (SEQ ID NO: 4)
X1X2GLPINQRFILVELSNHAELSVILAX4X5X6X1NAYVVGYRAGNSX3YFFHPDNQX2DAEAI

THLFTDX3
``` wherein both X1's are C, both X2's are C, or both X3's are C, X4 is L, F, C, M, A, T, S, W, Y, P, H, E, Q, D, N, K, or R, X5 is D, I, V, L, F, C, M, A, G, T, S, W, Y, P, H, E, Q, N, K, or R, X6 is V, I, F, C, M, A, G, T, W, Y, P, H, E, Q, D, N, K, or R, and wherein when both X1's are C, X6 is not I. In some embodiments, when both X1's are C, X5 is D or N and X6 is V, when both X2's are C, X5 is D and X6 is V or I or X5 is N and X6 is V, and when both X3's are C, X5 is D and X6 is V. In some embodiments, the amino acid molecule contains a second sequence that has at least 80, 81, 82, 83, 84, 85, 86, 87, 88, 89, 90, 91, 92, 93, 94, 95, 96, 97, 98, 99, or 100% sequence identity to

```
                                                    (SEQ ID NO: 5)
MIFPKQYPIINFTTAGATVQSYTNFIRAVRGRLTTGADVRHEIPVLPN, (SEQ ID NO: 6)
IFPKQYPIINFTTAGATVQSYTNFIRAVRGRLTTGADVRHEIPVLPN,
```

-continued

```
                                                    (SEQ ID NO: 7)
MVPKQYPIINFTTAGATVQSYTNFIRAVRGRLTTGADVRHEIPVLPN, (SEQ ID NO: 8)
MIFPKQYPIINFTTAGATVQSYTNFIRAVRGRLTVLPN, (SEQ ID NO: 9)
MVPKQYPIINFTTAGATVQSYTNFIRAVRGRLTVLPN, (SEQ ID NO: 10)
IFPKQYPIINFTTAGATVQSYTNFIRAVRGRLTVLPN,
or
                                                    (SEQ ID NO: 11)
IFPKQYPIINFTTAGATVQSYTNFIRAVRGRLTV
``` and/or a third sequence that has at least 80, 81, 82, 83, 84, 85, 86, 87, 88, 89, 90, 91, 92, 93, 94, 95, 96, 97, 98, 99, or 100% sequence identity to

```
                                                    (SEQ ID NO: 12)
QNRYTFAFGGNYDRLEQLAGNLRENIELGNGPLEEAISALYYYSTGGTQLPTLARSFIICIQMI

SEAARFQYIEGEMRTRIRYNRRS,
or
                                                    (SEQ ID NO: 13)
QNRYTFAFGGNYDRLEQLAGNLRENIELGNGPLEEAISALYYYSTGGTQLPTLARSFIICIQMIS

EAARFQYIEGEMRTRIRYNRRSA.
```

For example, in some embodiments, the polypeptides of the present invention have at least 80, 81, 82, 83, 84, 85, 86, 87, 88, 89, 90, 91, 92, 93, 94, 95, 96, 97, 98, 99, or 100% sequence identity to:

A. (SS)RTA 198:

```
                                                    (SEQ ID NO 14)
IFPKQYPIINFTTAGATVQSYTNFIRAVRGRLTTGADVRHEIPVLPNX1X2GLPINQRFILVELS

NHAELSVTLAX4X5X6X1NAYVVGYRAGNSX3YFFHPDNQX2DAEAITHLFTDX3QNRYTFAFGG

NYDRLEQLAGNLRENIELGNGPLEEAISALYYYSTGGTQLPTLARSFIICIQMISEAARFQYIEG

EMRTRIRYNRRS;
or
```

B. (SS)RTA 1-33/44-198:

```
                                                    (SEQ ID NO: 15)
IFPKQYPIINFTTAGATVQSYTNFIRAVRGRLTVLPNX1X2GLPINQRFILVELSNHAELSVTLA

X4X5X6X1NAYVVGYRAGNSX3YFFHPDNQX2DAEAITHLFTDX3QNRYTFAFGGNYDRLEQLAG

NLRENIELGNGPLEEAISALYYYSTGGTQLPTLARSFIICIQMISEAARFQYIEGEMRTRIRYNR

RS
``` wherein both X1's are C, both X2's are C, or both X3's are C, X4 is L, F, C, M, A, T, S, W, Y, P, H, E, Q, D, N, K, or R, X5 is D, I, V, L, F, C, M, A, G, T, S, W, Y, P, H, E, Q, N, K, or R, X6 is V, I, F, C, M, A, G, T, W, Y, P, H, E, Q, D, N, K, or R, and wherein when both X1's are C, X6 is not I. In some embodiments, when both X1's are C, X5 is D or N and X6 is V, when both X2's are C, X5 is D and X6 is V or I or X5 is N and X6 is V, and when both X3's are C, X5 is D and X6 is V.

As used herein, RTA198 R48C/T77C refers to SEQ ID NO:14, wherein when both X1's are C, X5 is D and X6 is V, RTA198 R48C/T77C/D75N refers to SEQ ID NO:14, wherein when both X1's are C, X5 is N and X6 is V, RTA198 V49C/E99C refers to SEQ ID NO:14, wherein when both X2's are C, X5 is D and X6 is V, RTA198 V49C/E99C/V76I refers to SEQ ID NO:14, wherein when both X2's are C, X5 is D and X6 is I, RTA198 V49C/E99C/D75N refers to SEQ ID NO:14, wherein when both X2's are C, X5 is N and X6 is V, and RTA198 A90C/V111C refers to SEQ ID NO:14, wherein when both X3's are C, X5 is D and X6 is V.

As used herein, RTA1-33/44-198 R48C/T77C refers to SEQ ID NO:15, wherein when both X1's are C, X5 is D and X6 is V, RTA1-33/44-198 R48C/T77C/D75N refers to SEQ ID NO:15, wherein when both X1's are C, X5 is N and X6 is V, RTA1-33/44-198 V49C/E99C refers to SEQ ID NO:15, wherein when both X2's are C, X5 is D and X6 is V, RTA1-33/44-198 V49C/E99C/V76I refers to SEQ ID NO:15, wherein when both X2's are C, X5 is D and X6 is I, RTA1-33/44-198 V49C/E99C/D75N refers to SEQ ID NO:15, wherein when both X2's are C, X5 is N and X6 is V, and RTA1-33/44-198 A90C/V111C refers to SEQ ID NO:15, wherein when both X3's are C, X5 is D and X6 is V.

As used herein, use of "(SS)" indicates an engineered disulfide bond. Thus, use of (SS) in conjunction with a polypeptide indicates that the polypeptide has been engineered to have a disulfide bond. For example, "(SS)RTA" refers to an RTA molecule which has been engineered to have a disulfide bond and includes (SS)RTA 198 and (SS) RTA1-33/44-198, such as RTA198 R48C/T77C and RTA1-33/44-198 R48C/T77C, for example. Similarly, use of (SS) in conjunction with a polynucleotide indicates that the polynucleotide encodes a polypeptide which has an engineered disulfide bond. As set forth herein, amino acid residues are referred to by their one letter codes (except for their three letter designations in the sequence listing submitted herewith).

The (SS)RTA polypeptides of the present invention need not be identical to those exemplified herein so long as the subject polypeptides are able to induce an immune response against RTA, ricin, or both, and exhibit a higher melting temperature than RTA 198 or RTA1-33/44-198 and/or a lower ability to self aggregate than RTA 198 or RTA1-33/44-198. For example, the (SS)RTA polypeptides according to the present invention include suitable variants which are those having insignificant changes such as a methionine as the first amino acid residue at the amino terminus, conservative amino acid substitutions, deletion of or insertion of up to about 10 amino acid residues in the linker or loop region of wt RTA, and co-translational or post-translational surface modifications such as the addition of covalently attached sugars or lipids. Insignificant changes refer to modifications in the amino acid sequence of a given (SS)RTA polypeptide that do not change the solubility, N-glycosidase-rRNA activity, or immunogenicity of the polypeptide.

Examples of suitable (SS)RTA variants include:

(SEQ ID NO: 16)
MIFPKQYPIINFTTAGATVQSYTNFIRAVRGRLTTGADVRHEIPVLPNX1X2GLPINQRFILVEL

SNHAELSVTLAX4X5X6X1NAYVVGYRAGNSX3YFFHPDNQX2DAEAITHLFTDX3QNRYTFAFG

GNYDRLEQLAGNLRENIELGNGPLEEAISALYYYSTGGTQLPTLARSFIICIQMISEAARFQYIE

GEMRTRIRYNRRS;

(SEQ ID NO: 17)
MIFPKQYPIINFTTAGATVQSYTNFIRAVRGRLTVLPNX1X2GLPINQRFILVELSNHAELSVTL

AX4X5X6X1NAYVVGYRAGNSX3YFFHPDNQX2DAEAITHLFTDX3QNRYTFAFGGNYDRLEQLA

GNLRENIELGNGPLEEAISALYYYSTGGTQLPTLARSFIICIQMISEAARFQYIEGEMRTRIRYN

RRS;

(SEQ ID NO: 18)
MVPKQYPIINFTTAGATVQSYTNFIRAVRGRLTTGADVRHEIPVLPNX1X2GLPINQRFILVELS

NHAELSVTLAX4X5X6X1NAYVVGYRAGNSX3YFFHPDNQX2DAEAITHLFTDX3QNRYTFAFGG

NYDRLEQLAGNLRENIELGNGPLEEAISALYYYSTGGTQLPTLARSFIICIQMISEAARFQYIEG

EMRTRIRYNRRS;

(SEQ ID NO: 19)
MVPKQYPIINFTTAGATVQSYTNFIRAVRGRLTVLPNX1X2GLPINQRFILVELSNHAELSVTLA

X4X5X6X1NAYVVGYRAGNSX3YFFHPDNQX2DAEAITHLFTDX3QNRYTFAFGGNYDRLEQLAG

NLRENIELGNGPLEEAISALYYYSTGGTQLPTLARSFIICIQMISEAARFQYIEGEMRTRIRYNR

RS;

-continued

```
                                                        (SEQ ID NO: 20)
IFPKQYPIINFTTAGATVQSYTNFIRAVRGRLTNX1X2GLPINQRFILVELSNHAELSVTLAX4X

5X6X1NAYVVGYRAGNSX3YFFHPDNQX2DAEAITHLFTDX3QNRYTFAFGGNYDRLEQLAGNLR

ENIELGNGPLEEAISALYYYSTGGTQLPTLARSFIICIQMISEAARFQYIEGEMRTRIRYNRRS;

(SEQ ID NO: 21)
MIFPKQYPIINFTTAGATVQSYTNFIRAVRGRLTTGADVRHEIPVLPNX1X2GLPINQRFILVEL

SNHAELSVTLAX4X5X6X1NAYVVGYRAGNSX3YFFHPDNQX2DAEAITHLFTDX3QNRYTFAFG

GNYDRLEQLAGNLRENIELGNGPLEEAISALYYYSTGGTQLPTLARSFIICIQMISEAARFQYIE

GEMRTRIRYNRRSA;
and (SEQ ID NO: 22)
MIFPKQYPIINFTTAGATVQSYTNFIRAVRGRLTVLPNX1X2GLPINQRFILVELSNHAELSVTL

AX4X5X6X1NAYVVGYRAGNSX3YFFHPDNQX2DAEAITHLFTDX3QNRYTFAFGGNYDRLEQLA

GNLRENIELGNGPLEEAISALYYYSTGGTQLPTLARSFIICIQMISEAARFQYIEGEMRTRIRYN

RRSA
``` wherein both X1's are C, both X2's are C, or both X3's are C, X4 is L, F, C, M, A, T, S, W, Y, P, H, E, Q, D, N, K, or R, X5 is D, I, V, L, F, C, M, A, G, T, S, W, Y, P, H, E, Q, N, K, or R, X6 is V, I, F, C, M, A, G, T, W, Y, P, H, E, Q, D, N, K, or R, and wherein when both X1's are C, X6 is not I. In some embodiments, when both X1's are C, X5 is D or N and X6 is V, when both X2's are C, X5 is D and X6 is V or I or X5 is N and X6 is V, and when both X3's are C, X5 is D and X6 is V.

Examples of unsuitable variants (and which are expressly excluded as being polypeptides according to the instant invention) include:

```
N141C/I192C:
                                                        (SEQ ID NO: 23)
IFPKQYPIINFTTAGATVQSYTNFIRAVRGRLTVLPNRVGLPINQRFILVELS

NHAELSVTLALDVTNAYVVGYRAGNSAYFFHPDNQEDAEAITHLFTDVQNRYTFAFGGNYDRLEQ

LAGNLRENIELGCGPLEEAISALYYYSTGGTQLPTLARSFIICIQMISEAARFQYIEGEMRTRCR

YNRRS,

R125C/A165C:
                                                        (SEQ ID NO: 24)
IFPKQYPIINFTTAGATVQSYTNFIRAVRGRLTVLPNRVGLPINQRFILVELS

NHAELSVTLALDVTNAYVVGYRAGNSAYFFHPDNQEDAEAITHLFTDVQNRYTFAFGGNYDCLEQ

LAGNLRENIELGNGPLEEAISALYYYSTGGTQLPTLCRSFIICIQMISEAARFQYIEGEMRTRIR

YNRRS,

R48C/T77C/V76I:
                                                        (SEQ ID NO: 25)
IFPKQYPIINFTTAGATVQSYTNFIRAVRGRLTVLPNCVGLPINQRFILV

ELSNHAELSVTLALDICNAYVVGYRAGNSAYFFHPDNQEDAEAITHLFTDVQNRYTFAFGGNYDR

LEQLAGNLRENIELGNGPLEEAISALYYYSTGGTQLPTLARSFIICIQMISEAARFQYIEGEMRT

RIRYNRRS,

E138C/P143C:
                                                        (SEQ ID NO: 26)
IFPKQYPIINFTTAGATVQSYINFIRAVRGRLTVLPNRVGLPINQRFILVELS

NHAELSVILALDVTNAYVVGYRAGNSAYFFHPDNQEDAEAITHLFTDVQNRYTFAFGGNYDRLEQ

LAGNLRENICLGNGCLEEAISALYYYSTGGTQLPTLARSFIICIQMISEAARFQYIEGEMRTRIR

YNRRS,
and
```

Q128C/A165C:

(SEQ ID NO: 27)
IFPKQYPIINFTTAGATVQSYTNFIRAVRGRLTVLPNRVGLPINQRFILVELS

NHAELSVTLALDVTNAYVVGYRAGNSAYFFHPDNQEDAEAITHLFTDVQNRYTFAFGGNYDRLEC

LAGNLRENIELGNGPLEEAISALYYYSTGGTQLPTLCRSFIICIQMISEAARFQYIEGEMRTRIR

YNRRS as these polypeptides either had no effect on the apparent melting temperature or had a lower apparent melting temperature as compared to RTA 1-33/44-198. Other unsuitable variants include those which have a greater tendency to self aggregate than RTA 198 or RTA1-33/44-198.

Methods known in the art, including those disclosed herein, may be conducted to determine whether a (SS)RTA variant is suitable, and thereby falls within the scope of the (SS)RTA polypeptides as set forth in the claims, or unsuitable, and thereby falls outside the scope of the (SS)RTA polypeptides as set forth in the claims. See e.g. Compton et al. (2011) Proteins: Structure, Function, and Bioinformatics 79:1048-1060, which is herein incorporated by reference.

For example, to compare the relative amounts of protein aggregation in various solutions, the amounts and types of aggregates formed by the variants may be quantified as a function of protein concentration and time under various conditions such as fixed buffer composition, ionic strength, and pH. A combination of analytical size-exclusion chromatography (SEC) may be used with on-line multi-angle light scattering (MALS) detection which provides a measure of the molar mass of proteins in solution because the light scattering response is directly proportional to the weight-averaged molar mass (Mw) of the protein sample multiplied by the sample concentration. For example, solutions of protein samples at a concentration of about 0.4 to about 1.5 mg/ml in 0.067 M Na/K phosphate, pH 7.5 are separated using standard high performance liquid chromatographic methodology with a flow rate of about 0.5 to about 1.0 ml/min. Protein species are detected with an in-line standard UV/VIS HPLC detector, and the relative refractive indices of the sample components are determined from an in-line interferometric refractometer. Light scattering data are collected at many wavelengths, averaged, and evaluated using an in-line MALS instrument. Aggregates are quantified by molar mass for each protein sample.

To compare the relative protein folding stability of a given variant versus RTA 198 and/or RTA1-33/44-198 the following may be conducted. Relative protein folding stability is measured indirectly by comparing the amount of energy (proportional to temperature) required to unfold each polypeptide under various conditions of ionic strength or pH. The extent of protein unfolding is assessed indirectly by circular dichroism (CD) spectroscopy. Briefly, CD scans of protein samples are performed in a spectropolarimeter, fitted with peltier thermal control unit, using 0.2 mm and 1 cm path length quartz cuvettes, respectively, for near and far UV measurements. Solutions of purified polypeptide are used at a concentration of about 0.5 mg/ml in 0.067 M Na/K phosphate, pH 7.5. The initial scans provide baseline spectra and corroborate that the protein samples are folded. Subsequently, protein samples are intentionally and slowly unfolded by increasing the cuvet temperature by means of the thermal control unit. Temperature-induced changes in protein secondary structure are assessed indirectly by monitoring the change in mean residue ellipticity at 222 nm. From these data, one may calculate and compare the temperature ($T_m$) at which 50% of the protein is unfolded. If the novel RTA polypeptides are found to fold and unfold reversibly, then one may also calculate and compare the thermodynamic and enthalpic constants for protein folding.

To evaluate how the biophysical properties of a variant may vary as a function of storage time (such as over the course of 24 months) and storage temperature (such as at about 2 to about 8, 25 and 40° C.) in different storage formulations the following assay may be conducted. The number of possible storage formulations is very large; therefore, only a subset of formulations using a sparse matrix that isolates selected variables are tested. These variables might include the buffer composition, the ionic strength, the pH, or the presence or absence of preferred adjuvants. Biophysical properties of the novel RTA polypeptides to be observed under different storage conditions may include, relative molecular mass of polypeptides, apparent isoelectric point of polypeptides (net charge), extent of self-aggregation, protein folding stability, and exposure of hydrophobic surfaces. These can be evaluated as described using SDS-PAGE, native PAGE, isoelectric focusing, light scattering, circular dichroism spectroscopy and ANS dye binding.

To determine the precise three-dimensional structures of a given variant near atomic resolution single crystal, macromolecular X-ray crystallographic methods and NMR may be used. Protein crystals of a given variant are obtained using the hanging-drop vapour-diffusion method, and a sparse matrix of crystallization conditions. Protein crystals are flash-frozen in liquid nitrogen prior to data collection at 100° K. Data may be collected using a suitable X-ray diffraction apparatus with accompanying detectors. Structure solution can be attempted using molecular replacement and the coordinates of a comparable RTA molecule (for example, Protein Databank, PDB, entry 1IL3 or an (SS)RTA derivative (for example, PDB entry 3LC9 or 3MK9,) as a starting model. The structures may be refined by a combination of simulated annealing and molecular dynamics with a maximum likelihood target function, using the CNS program suite or comparable semi-automated protein structure refinement software packages. See Adams et al. (1997) PNAS USA 94:5018-23; and Brunger et al. (1998) Acta Cryst. D54, 905-921.

The (SS)RTA polypeptides of the present invention are stable, non-toxic, and retain those portions of the molecule that have been shown previously to elicit an immune response in a human subject. Thus, the (SS)RTA polypeptides of the present invention may be used to prevent or treat systemic side effects of locally administered ricin toxin. In preferred embodiments, the (SS)RTA polypeptides of the present invention are capable providing a protective immune response in a subject. Preferably, the subject is mammalian, more preferably, the subject is human. As used herein, an "immune response" refers to a humoral or cellular response caused by exposure to an antigenic substance combined in some cases with a suitable adjuvant substance. Thus, an immune response against ricin or "ricin immune response"

refers to a humoral or cellular response in a subject that is caused by exposing the subject to an antigenic substance such as polypeptides of the present invention. A "protective immune response" against ricin refers to humoral immune responses, cellular immune responses, or both, that are sufficient to inhibit or prevent ricin intoxication in a subject.

The (SS)RTA polypeptides of the present invention may also be modified to provide a variety of desired attributes, e.g. improved pharmacological characteristics, while increasing or at least retaining substantially all of the immunological activity of the RTA. By using conventional methods in the art, one of ordinary skill will be readily able to make a variety of polypeptides having mutated linker regions and then screen the polypeptides for stability, toxicity, and immunogenicity according to the present invention.

Additionally, single amino acid substitutions, deletions, or insertions can be used to determine which residues are relatively insensitive to modification. Amino acid substitutions are preferably made between relatively neutral moieties, such as alanine, glycine, proline, and the like. Substitutions with different amino acids, of either D or L isomeric forms, or amino acid mimetics can be made. The number and types of substitutions, deletions, and insertions depend on the functional attributes that are sought such as hydrophobicity, immunogenicity, three-dimensional structure, and the like.

An "amino acid mimetic" as used herein refers to a moiety other than a naturally occurring amino acid residue that conformationally and functionally serves as a suitable substitute for an amino acid residue in a polypeptide of the present invention. A moiety is a suitable substitute for an amino acid residue if it does not interfere with the ability of the peptide to elicit an immune response against ricin. Examples of amino acid mimetics include cyclohexylalanine, 3-cyclohexylpropionic acid, L-adamantyl alanine, adamantylacetic acid, and the like. See e.g. Morgan & Gainor (1989) Ann. Repts. Med. Chem. 24:243-252.

Individual amino acid residues may be incorporated in the polypeptides of the present invention with peptide bonds or peptide bond mimetics. A peptide bond mimetic include peptide backbone modifications of the amide nitrogen, the α-carbon, amide carbonyl, complete replacement of the amide bond, extensions, deletions or backbone crosslinks. See e.g. Spatola (1983) CHEMISTRY AND BIOCHEMISTRY OF AMINO ACIDS, PEPTIDES AND PROTEINS, Vol. VII, Weinstein ed. The (SS)RTA polypeptides of the present invention may include an additional methionine as the first amino acid residue on the protein amino terminus. The (SS)RTA polypeptides may be truncated by up to about ten (10) amino acid residues from the carboxyl terminus of (SS)RTA198 (SEQ ID NO:14), (SS)RTA1-33/44-198 (SEQ ID NO:15), or the like. Similarly, up to about ten (10) amino acid residues from wt RTA bordering the hydrophobic loop, amino acid residues at about position 34 to about 43 may be deleted. Additionally, co-translational or post-translational surface modifications, such as the addition of covalently attached sugars or lipids, may be made to the polypeptides of the present invention.

In some embodiments, the (SS)RTA polypeptides of the present invention have substantial identity, e.g. at least 80, 81, 82, 83, 84, 85, 86, 87, 88, 89, 90, 91, 92, 93, 94, 95, 96, 97, 98, 99, or 100% sequence identity, to the amino acid sequence set forth in SEQ ID NOs:4, 14 or 15. As used herein "sequence identity" means that two sequences are identical over a window of comparison. The percentage of sequence identity is calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity. In some embodiments, the amino acid residues in corresponding positions are identical or differ only by "conservative amino acid substitutions".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan).

The (SS)RTA polypeptides of the present invention may be made by conventional methods known in the art. The (SS)RTA polypeptides of the present invention may be manually or synthetically synthesized using conventional methods and devices known in the art. See e.g. Stewart and Young (1984) SOLID PHASE PEPTIDE SYNTHESIS, 2 ed. Pierce, Rockford, Ill., which is herein incorporated by reference. The parent polypeptide, e.g. Ricin, RTA, RTA 198, or RTA1-33/44-198, and the polynucleotide encoding the parent polypeptide may be obtained by conventional methods. See U.S. Pat. Nos. 5,547,867 and 6,869,787; Olson et al. (2004) Protein Eng Des Sel 17:91-397, which are herein incorporated by reference. Then the parent polypeptide and/or the parent polynucleotide may be further modified to result in the desired (SS)RTA using methods known in the art. The polypeptides may be purified from natural sources using conventional protein purification techniques such as reverse phase high-performance liquid chromatography (HPLC), ion-exchange or immunoaffinity chromatography, filtration or size exclusion, or electrophoresis. See Olsnes & Pihl (1973) Biochem. 12(16):3121-3126; and see e.g. Scopes (1982) PROTEIN PURIFICATION, Springer-Verlag, NY, which are herein incorporated by reference.

In some embodiments, the polynucleotide encoding an (SS)RTA according to the present invention is codon-optimized using methods known in the art. For example, one skilled in the art may start a codon-optimized sequence for RTA1-33/44-198 such as (SEQ ID NO: 28)
```
atgatcttcccgaaacagtacccgatcatcaacttcaccaccgcaggtgcaaccgttcagtctta caccaacttcatccgtgcagttcgtggtcgcctgaccgttctgccgaaccgtgttggtctgccga tcaaccagcgtttcatcctggtagaactgtctaaccacgcagaactgtctgttaccctggcactg gacgttaccaacgcgtacgtagtgggctaccgtgcgggtaactctgcatacttcttccacccaga
```

```
caaccaggaggacgcagaagcaatcacccacctgttcaccgacgttcagaaccgttacaccttcg cgttcggtggcaactacgatcgtctggaacagctggcaggtaacctgcgtgagaacatcgaactg ggtaacggtccgctggaagaggcgatctctgcgctgtactactattctaccggtggtacccagct gccgaccctggcgcgttctttcatcatctgcatccagatgatctctgaagcggcacgtttccagt acatcgaaggtgaaatgcgtacccgtatccgttacaaccgtcgttcttag
``` and then further modify the sequence to result in the desired (SS)RTA such as RTA1-33/44-198 R48C/T77C, RTA1-33/44-198 R48C/T77C/D75N, RTA1-33/44-198 V49C/E99C, RTA1-33/44-198 V49C/E99C/V76I, RTA1-33/44-198 V49C/E99C/D75N, and RTA1-33/44-198 A90C/V111C. In some embodiments, the (SS)RTA according to the present invention is made from a codon-optimized polynucleotide.

Prior art methods for purifying RTA rely upon the separation of RTA and RTB by disulfide reduction and subsequence lectin binding, or affinity chromatography with specialized affinity resins. See Fulton et al. (1986) J. Biol. Chem. 261: 5314-5319 and Emmanuel et al. (1988) Anal. Biochem. 173: 134-141, which are herein incorporated by reference. Since the biophysical properties of the (SS)RTA polypeptides, i.e. isoelectric points, are different from wt RTA, the polypeptides of the present invention may be purified without the use of sulfhydryl reduction or costly, specialized affinity resins. Specifically, conventional ion-exchange chromatography based upon the isoelectric points of the (SS)RTA polypeptides may be used to purify the (SS)RTA polypeptides of the present invention. In embodiments where the (SS)RTA polypeptide may be crystallized, known purification methods based on crystallization may be used to purify and/or further purify such polypeptides. Alternatively, the (SS)RTA polypeptides of the present invention may be made by conventional recombinant DNA techniques known in the art. Thus, the present invention provides (SS)RTA polynucleotides that encode the (SS)RTA polypeptides of the present invention.

In some embodiments, the (SS)RTA polypeptides and/or the (SS)RTA nucleic acid molecules according to the present invention are isolated and/or purified. An "isolated" nucleic acid molecule or polypeptide refers to a nucleic acid molecule or polypeptide that is in an environment that is different from its native environment in which the nucleic acid molecule or polypeptide naturally occurs. Isolated nucleic acid molecules or polypeptides includes those having nucleotides or amino acids flanking at least one end that is not native to the given nucleic acid molecule or polypeptide. For example, sequence X is inserted at a given end of sequence A which does not natively have sequence X at the given end. Sequence X is thus considered to be "isolated".

As used herein, a "purified" polypeptide or nucleic acid molecule means that some or all of the components in the composition from which the polypeptide or the nucleic acid molecule was obtained have been removed. In some embodiments, the polypeptides of the present invention are substantially purified. As used herein, a "substantially purified" compound refers to a compound that is removed from its natural environment and is at least about 60% free, preferably about 75% free, and most preferably at least about 90, 91, 92, 93, 94, 95, 96, 97, 98, or 99% free from other macromolecular components with which the compound is naturally associated.

A (SS)RTA polynucleotide that encodes a polypeptide having substantial identity to a (SS)RTA polypeptide according to the instant invention, e.g. SEQ ID NO:4, can be made by introducing one or more nucleotide substitutions, insertions, or deletions into the nucleotide sequence that encodes SEQ ID NO:4 such that one or more amino acid substitutions, insertions, or deletions are introduced into the encoded polypeptide. Mutations can be introduced by standard techniques, such as site-directed mutagenesis and PCR-mediated mutagenesis and/or linear amplification methods known in the art may be used. The (SS)RTA polynucleotide is then inserted in to a vector such as a cloning vector or an expression vector. An expression vector allows the polypeptide to be expressed when present in a host. Either the expression vector or the host may comprise the regulatory sequences necessary for expression of the polypeptide. Where the regulatory sequences are within the expression vector, the regulatory sequences are operatively linked to the sequence encoding the polypeptide. As used herein, "operably linked" means that the nucleotide sequence of interest is linked to at least one regulatory sequence in a manner that allows the polypeptide to be expressed in an in vitro transcription/translation system or in a host cell. Regulatory sequences include promoters, enhancers and other expression control elements (e.g., polyadenylation signals). See e.g. Goeddel (1990) GENE EXPRESSION TECHNOLOGY: METHODS IN ENZYMOLOGY, Academic Press, San Diego, Calif., which is herein incorporated by reference.

It will be appreciated by those skilled in the art that the design of the expression vector can depend on such factors as the choice of the host cell to be transformed, the desired expression levels of the polypeptide, the compatibility of the host cell and the expressed polypeptide, and the like. The vectors can be designed for expressing the polypeptides of the present invention of in prokaryotic or eukaryotic host cells such as bacterial cells, insect cells, plant cells, yeast cells, or mammalian cells. In preferred embodiments, the host cells are bacterial cells. Suitable host cells are discussed further in Goeddel supra; Baldari, et al. (1987) EMBO J. 6:229-234; Kurjan and Herskowitz (1982) Cell 30:933-943; Schultz, et al. (1987) Gene 54:113-123; Smith, et al. (1983) Mol. Cell. Biol. 3:2156-2165; Lucklow and Summers (1989) Virology 170:31-39; Seed (1987) Nature 329:840; Kaufman, et al. (1987) EMBO J. 6:187-6195; Sambrook, et al. (2000) MOLECULAR CLONING: A LABORATORY MANUAL. Cold Spring Harbor Laboratory, Cold Spring Harbor Laboratory Press, Cold Spring Harbor, N.Y.; and those available from Invitrogen Corporation, San Diego, Calif., such as pYES2 and picZ, all of which are herein incorporated by reference.

Thus, the present invention also provides host cells comprising (SS)RTA polynucleotides of the present invention. Host cells include the progeny or potential progeny of the primary cell in which the polynucleotide was introduced. Because certain modifications may occur in succeeding generations due to either mutation or environmental influences, such progeny may not, in fact, be identical to the parent cell, but are still included within the scope and meaning of host cell.

A (SS)RTA polypeptide of the present invention may be used to prepare antibodies against ricin by immunizing a suitable subject, e.g., rabbit, goat, mouse or other mammal with the polypeptide by conventional methods known in the art. Large quantities of neutralizing antibodies could be generated and then used as an antidote for ricin intoxication. See Lemley et al. (1994) Hybridoma 13(5):417-427 and U.S. Pat. No. 5,626,844, which are herein incorporated by reference. The antibodies raised against the (SS)RTA polypeptides of the present invention may be used to prevent or treat systemic side effects of locally administered ricin toxin. Thus, the present invention also provides antibodies that are raised against or derived from the (SS)RTA polypeptides of the present invention, and methods of using thereof.

Antibodies of the present invention may be produced by conventional methods known in the art. See e.g. Coligan (1991) CURRENT PROTOCOLS IN IMMUNOLOGY. Wiley/Greene, NY; and Harlow and Lane (1989) ANTIBODIES: A LABORATORY MANUAL, Cold Spring Harbor Press, NY; Stites, et al. (1986) BASIC AND CLINICAL IMMUNOLOGY. 4th ed. Lange Medical Publications, Los Altos, Calif.; Goding (1986) MONOCLONAL ANTIBODIES: PRINCIPLES AND PRACTICE. 2d ed. Academic Press, New York, N.Y.; and Kohler and Milstein (1975) Nature 256:495-497, which are herein incorporated by reference. Therapeutic antibodies may be produced specifically for clinical use in humans by conventional methods known in the art. See Chadd & Chamow (2001) Curr. Opin. Biotechnol. 12:188-194 and references therein, all of which are herein incorporated by reference. The present invention has the advantage of allowing safe exposure of subjects, such as humans, to the RTA neutralizing epitope. Thus, the present invention allows for the safe in vivo production of RTA antibodies directly in subjects.

As used herein, "antibody" refers to immunoglobulin molecules and immunologically active portions that comprise an antigen binding site which specifically binds an antigen, such as ricin or an (SS)RTA according to the present invention. Examples of immunologically active portions of immunoglobulin molecules include F(ab) and F(ab')$_2$ fragments which may be generated by treating the antibody with an enzyme such as pepsin. As used herein, an "antibody" can be an intact immunoglobulin or a well characterized fragment thereof which may be produced by digestion with various peptidases or recombinant techniques known in the art. See Fundamental Immunology, W. E. Paul, ed., Raven Press, New York (1999). The term "antibody" also includes single chain antibodies, e.g. single chain Fv (sFv or scFv) antibodies in which a variable heavy and a variable light chain are joined together (directly or through a peptide linker) to form a continuous polypeptide. Polyclonal and monoclonal antibodies against the (SS)RTA polypeptides of the present invention may be made by conventional methods known in the art.

The (SS)RTA polypeptides, (SS)RTA polynucleotides, or antibodies of the present invention may be administered, preferably in the form of pharmaceutical compositions, to a subject. Preferably the subject is mammalian, more preferably, the subject is human. Preferred pharmaceutical compositions are those comprising at least one immunogenic composition against ricin, RTA, or both, in an immunogenic amount or a therapeutically effective amount, and a pharmaceutically acceptable vehicle. The immunogenic composition may be an active immunizing agent, such as a (SS)RTA polypeptide of the present invention, or a passive immunizing agent, such as an antibody raised against the (SS)RTA polypeptide of the present invention. The immunogenic composition may elicit an immune response that need not be protective or the immunogenic composition may provide passive immunity. A vaccine elicits a local or systemic immune response that is protective against subsequent challenge by the immunizing agent such as the (SS)RTA polypeptides of the present invention, or an immunologically cross-reactive agent, such as ricin. Conventional methods in the art may be used to determine the feasibility of using the (SS)RTA polypeptides of the present invention as vaccines against ricin intoxication. Accordingly, as used herein, an "immunogenic composition" can refer to vaccines as well as antibodies. A protective immune response may be complete or partial, i.e. a reduction in symptoms as compared with an unvaccinated mammal.

Thus, the present invention provides immunogenic compositions comprising at least one (SS)RTA polypeptide and/or at least one antibody raised against a (SS)RTA polypeptide of the present invention that may be used to immunize a subject against ricin by methods known in the art. See U.S. Pat. No. 5,453,271, which is herein incorporated by reference. As used herein, an "immunogenic amount" is an amount that is sufficient to elicit an immune response in a subject and depends on a variety of factors such as the immunogenicity of the polypeptide, the manner of administration, the general state of health of the subject, and the like. The typical immunogenic amounts for initial and boosting immunization for therapeutic or prophylactic administration ranges from about 0.01 mg to about 0.1 mg per about 65-70 kg body weight of a subject. For example, the typical immunogenic amount for initial and boosting immunization for therapeutic or prophylactic administration for a human subject ranges from about 0.01 mg to about 0.1 mg. Examples of suitable immunization protocols include initial immunization injections at time 0 and 4 or initial immunization injections at 0, 4, and 8 weeks, which initial immunization injections may be followed by further booster injections at 1 or 2 years.

As used herein, a "therapeutically effective amount" refers to an amount that may be used to treat, prevent, or inhibit a given condition, such as ricin intoxication, in a subject as compared to a control. Again, the skilled artisan will appreciate that certain factors may influence the dosage required to effectively treat a subject, including the severity of ricin exposure, previous treatments, the general health and age of the subject, and the like. A therapeutically effective amount may be readily determined by conventional methods known in the art. It should be noted that treatment of a subject with a therapeutically effective amount of a given substance, e.g. a (SS)RTA polypeptide according to the present invention, may be administered as a single dose or as a series of several doses.

The pharmaceutical compositions may include an adjuvant. As used herein, an "adjuvant" refers to any substance which, when administered with or before a pharmaceutically active agent, such as a (SS)RTA polypeptide, aids the pharmaceutically active agent in its mechanism of action. Thus, an adjuvant in a vaccine is a substance that aids the immunogenic composition in eliciting an immune response. Suitable adjuvants include incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, nor-MDP), N-acetylmuramyl-Lalanyl-D-isoglutaminyl-L-alanine-2-(1'-2'-dipa-lmitoyl-sn-glycero-3-hydroxyphosphoryloxy)-ethylamine (CGP 19835A, MTP-PE), and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by conventional methods in the art.

The compositions of the present invention may be administered to a subject by any suitable route including oral, transdermal, intranasal, inhalation, intramuscular, and intravascular administration. It will be appreciated that the preferred route of administration and pharmaceutical formulation will vary with the condition and age of the subject, the nature of the condition to be treated, the therapeutic effect desired, and the particular polypeptide, polynucleotide, or antibody used.

As used herein, a "pharmaceutically acceptable vehicle" or "pharmaceutically acceptable carrier" refers to and includes any and all solvents, dispersion media, coatings, antibacterial and antifungal agents, isotonic and absorption delaying agents, and the like, that are compatible with pharmaceutical administration. Pharmaceutically acceptable vehicles include those known in the art. See e.g. REMINGTON: THE SCIENCE AND PRACTICE OF PHARMACY. $20^{th}$ ed. (2000) Lippincott Williams & Wilkins. Baltimore, Md., which is herein incorporated by reference.

The pharmaceutical compositions of the present invention may be provided in dosage unit forms. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The formulations of the compositions of the present invention may be optimized for increased stability and efficacy using methods known in the art. See e.g. Carra et al. (2007) Vaccine 25:4149-4158, which is herein incorporated by reference.

Toxicity and therapeutic efficacy of the (SS)RTA polypeptides, polynucleotides, and antibodies according to the instant invention and compositions thereof can be determined by standard pharmaceutical procedures in cell cultures or experimental animals. For example, one may determine the lethal dose of toxin, $LCt_{50}$ (the dose expressed as concentration of toxin×exposure time that is lethal to 50% of the population) or the $LD_{50}$ (the dose lethal to 50% of the population), and the $ED_{50}$ (the dose therapeutically effective in 50% of the population) by conventional methods in the art. The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The present invention also provides (SS)RTA polypeptides, (SS)RTA polynucleotides, antibodies, and/or compositions thereof provided in kits along with instructions for use. A kit comprising a pharmaceutical composition may include the pharmaceutical composition as a single dose or multiple doses. The kit may include a device for delivering the (SS) RTA polypeptides, (SS)RTA polynucleotides, antibodies, and/or compositions thereof. The device may be a multi-chambered syringe for intramuscular delivery, a microneedle or set of microneedle arrays for transdermal delivery, a small balloon for intranasal delivery, or a small aerosol generating device for delivery by inhalation.

Ricin exposure is presently detected by medical history and symptoms, and is confirmed by antibody- or activity-based measurements of ricin in bodily fluids. Ricin detection or medical diagnosis of ricin exposure, therefore, may based upon immunoassays utilizing the antibodies or (SS)RTA polypeptides of the present invention or combinations thereof. Since a subject may be safely exposed to the (SS) RTA polypeptides of the present invention, exposure to ricin may be determined by detecting antibodies which recognize one or more (SS)RTA polypeptides in a subject in vivo. Additionally, as the (SS)RTA polypeptides of the present invention are relatively non-toxic and safe, immunoassays utilizing the polypeptides of the present invention for detecting antibodies against ricin would be also be safe. Thus, the present invention provides diagnostic assays for detecting ricin toxin, exposure to ricin, or both. The diagnostic assays may comprise the (SS)RTA polypeptides of the present invention, antibodies of the present invention, or a combination thereof. The diagnostic assays may be provided in the form of kits that may be used outside of a laboratory setting, such as in the field.

As disclosed herein, the (SS)RTA polypeptides of the present invention are fundamentally superior as immunogenic compositions such as ricin vaccines as compared ricin toxoid, wt RTAs, dgRTAs, RTA 198 and RTA 1-33/44-198 as the (SS)RTA polypeptides do not include RTB, lack detectable N-glycosidase-rRNA activity or exhibit reduced N-glycosidase-rRNA activity, exhibit greater thermal stability and storage stability, and exhibit a lower degree of aggregate formation as compared to controls, e.g. RTA 198 and RTA 1-33/44-198. As used herein, "detectable" N-glycosidase-rRNA activity refers to N-glycosidase-rRNA activity that may be detected by assays conventional in the art. See Hale (2001) Pharmacol. & Toxicol. 88:255-260, and Langer et al. (1996) Anal. Biochem. 243:150-153, both of which are herein incorporated by reference. These conventional assays routinely detect the ribosome inactivating activity of native RTA at toxin concentrations of 0.1 to 0.5 nM. Thus, the (SS)RTA polypeptides of the present invention that lack detectable N-glycosidase-rRNA activity refers to (SS)RTA polypeptides that do not exhibit ribosome inactivating activity at concentrations of less than about 0.5 nM, preferably, less than about 0.1 nM.

In some embodiments, the (SS)RTA polypeptides of the present invention have an aqueous solubility that is greater than the aqueous solubility of wt RTA, RTA 198 and/or RTA 1-33/44-198 as evidenced by high expression yields in the soluble fraction and by the absence of protein aggregation or precipitation upon storage in physiological saline solutions. Methods known in the art such as SDS-PAGE and isoelectric focusing may be used to determine the solubility and aggregation of polypeptides according to the present invention. In some embodiments, the (SS)RTA polypeptides of the present invention are more homogenous than dgRTA as the polypeptides may be consistently expressed and substantially purified in substantially the same manner as RTA 198 and RTA1-33/

44-198. See U.S. Pat. No. 6,869,787; Olson et al. (2004) Protein Eng Des Sel 17:91-397, which are herein incorporated by reference.

The following Examples are intended to illustrate, but not to limit the present invention.

Materials

Q SEPHAROSE, SP SEPHAROSE and PD-10 columns were purchased from GE Healthcare Life Sciences (Amersham Pharmacia, Piscataway, N.J.). All chemicals were purchased from Sigma. QuikChange™ kits were purchased from Stratagene. Plasmid purification kits were purchased from Qiagen (Hilden, Germany). BUGBUSTER® PROTEIN EXTRACTION REAGENT was from Novagen (Darmstadt, Germany). Syringe filters (0.1 μm) were purchased from Millipore. *E. coli* BL-21 (DE3) cells were purchased from Invitrogen (Carlsbad, Calif.). CRYSTAL SCREEN CRYO SOLUTION NUMBER 31 was obtained from Hampton Research (Aliso Viejo, Calif.). The PROTOBLOT® II AP SYSTEM mouse immunoblotting kit was purchased from Promega (Madison, Wis.).

Site-Directed Mutagenesis

Construction and purification of RTA198 and RTA1-33/44-198 was performed as described previously. See Olson et al. (2004) Protein Eng Des Sel 17:91-397; and U.S. Pat. No. 6,869,787, which are herein incorporated by reference. Site directed mutagenesis was done using the QUIKCHANGE™ kit as directed. Plasmid DNA was purified and sequenced using methods known in the art to verify that only the intended mutations had been introduced into the gene sequence. The DNA was then transformed into *E. coli* BL21(DE3) for protein expression using methods known in the art.

Protein Expression and Purification

*E. coli* were grown in LB media containing kanamycin (50 μg/ml) at 37° C. to a cell density of 0.8-1.0 $OD_{600}$. Cultures were induced with IPTG (0.2 mM) for 18-20 hours at 17° C. Cells pellets were resuspended in 50 ml of lysis buffer (50 mM sodium phosphate buffer, pH 7.3, 2 mM EDTA, 30% BUGBUSTER®) and sonicated, 30 seconds on/30 seconds off, for a total of 2 minutes. The lysate was clarified by centrifugation at 10,000 rpm for 1 h at 4° C. The supernatant was loaded onto a Q SEPHAROSE column equilibrated with 50 mM sodium phosphate buffer, 2 mM EDTA, pH 7.3, and the flow through was collected. Fractions containing the protein (about 22 kDa) were combined and dialyzed overnight at 4° C. against 1 L of 50 mM MES, 2 mM EDTA, pH 6.4. Dialyzed protein was loaded onto an SP SEPHAROSE column equilibrated with 50 mM MES, 2 mM EDTA, pH 6.4. Protein was eluted from the column using a 0-250 mM sodium chloride gradient, and was analyzed using SDS-PAGE. The fractions containing a single band on SDS-PAGE gels were combined and dialyzed into 10 mM phosphate buffer saline, pH 7.4.

Thiol Titrations

The stock of each protein (0.85-1.1 mg/ml) was divided into 50, 100, 150, and 200 μl aliquots and incubated in a water bath at 100° C. for 2.5 min. Tubes were then allowed to cool on ice until cold (about 5 min), followed by centrifugation for 5 sec to remove condensation from lid. Next 25 μl of a 20 mM stock of DTNB was mixed into each aliquot. The appropriate amount of 10 mM phosphate buffered saline, pH 7.4, was added to bring the contents of each tube to a final volume of 1 ml. The tubes were then incubated at room temperature without light for 20 min. After centrifugation at 14,000 g to pellet denatured protein, each reaction was transferred into a clean cuvette and the absorbance at 412 nm was read.

Protein Aggregation

Purified protein was sterile filtered using a 0.1 μm syringe filter. Protein was divided into 0.5 ml aliquots and incubated at 37° C. At various time intervals over the course of 61 days, four of the aliquots were removed from incubation. Three of these aliquots were centrifuged at maximum speed to pellet the protein aggregates. The absorbance at 280 nm was measured for each and the amount of protein remaining in solution was determined.

Thermal Denaturation Curves

Thermal denaturation (2° C./min) was monitored using a JASCO 810 Circular Dichroism (CD) spectrophotometer fitted with a PELTIER temperature controller. Concentrations of protein solutions (about 0.2 mg/ml in phosphate buffered saline, pH 7.4) were determined by UV-vis using a calculated extinction coefficient ($\epsilon$=18005 $M^{-1}cm^{-1}$). Melting curves were measured between 10-80° C. by monitoring the change in ellipticity at 222 nm. The melting temperature was determined from a four parameter fit of the averaged signal from two scans versus temperature.

Crystallization of RTA 1-33/44-198 R48C/T77C and V49C/E99C

Stabilization of the loop region of RTA 1-33/44-198, by R48C/T77C or V49C/E99C facilitated protein crystallization. It is noted that RTA 1-33/44-198 resulted in brittle crystals.

Specifically, the proteins were additionally purified using a G-200 SUPERDEX column (1×39 cm) equilibrated with 50 mM MES pH 6.4 and 200 mM NaCl. Orthorhombic 1222 crystals were grown in HAMPTON CRYSTAL SCREEN CRYO SOLUTION #31 (0.17 M Ammonium Sulfate, 25.5% PEG 4000, 15% glycerol) at room temperature by hanging-drop using a 1:1 ratio of protein to precipitant. It is noted that HAMPTON CRYSTAL SCREEN CRYO SOLUTION #30 was also used and resulted in crystals. Sheet like crystals were obtained over 1-3 months and were frozen in PARATONE-N.

Structure of the RTA 1-33/44-198 R48C/T77C and V49C/E99C

The crystals were diffracted out to 2.1 Å. Data out to 2.3 Å were used for structure determination.

Superposition of RTA 1-33/44-198 R48C/T77C with RIVAX protein yielded a r.m.s.d. of 1.05 Å over 169 $C_{alpha}$, suggesting that the three dimensional structure does not significantly differ from RiVax. Only residues in the C-terminus and a loop between residues 122-127 (at a crystal packing interface) of RTA 1-33/44-198 R48C/T77C appear to be different from RIVAX. In RIVAX residues 173-179 form part of a sharp turn in between two helical segments, whereas in RTA 1-33/44-198 R48C/T77C these residues form a helix without a turn. These residues are of particular significance since they form a portion of the B-cell epitope.

The disulfide bond was only partially covered in density in a 2Fo-Fc map (data not shown), thereby suggesting that residues in the loop are highly mobile and that the disulfide bond may only be partially formed in the crystal. Density surrounding loop residues 37-41 was not observed. The $\chi_1$, $\chi_2$, $\chi_3$, $\chi_1'$, and $\chi_2'$ torsion angles were −62.6, 161.6, 51.8, 107.4, and 174.2 degrees respectively, thereby suggesting right-handed disulfides. See Katz & Kossiakoff (1986) J. Biol. Chem. 261:15480-15485, which is herein incorporated by reference. The $\chi$3 angle differs significantly from those typically observed (92-103 degrees). The $\chi_2$ angle also differs (expected range=43 to 84 degrees) and suggests a strained conformation. Table 1 provides the X-ray crystallography data collection and refinement summary statistics.

TABLE 1

X-ray crystallography data collection and refinement summary statistics

|  | RTA_1-33/44-198 R48C/T77C | RTA_1-33/44-198 V49C/E99C |
|---|---|---|
| Space group | I222 | I222 |
| Unit Cell Dimensions (Å) | a = 51.5, b = 72.3, c = 94.2 | a = 51.7, b = 72.8, c = 96.4 |
| Wavelength (Å) | 1.54 | 1.54 |
| Resolution Range (Å)[a] | 57.4-2.3 (2.38-2.28) | 58.1-2.1 (2.17-2.08) |
| Unique Reflections | 8,333 (979) | 10,903 (1,009) |
| $R_{sym}$[b] | 0.098 (0.385) | 0.054 (0.326) |
| I/σI | 19.05 (5.52) | 20.18 (3.88) |
| Completeness | 100.0 (100.0) | 96.6 (77.1) |
| Redundancy | 16.0 (11.9) | 9.6 (3.0) |
| Refinement Statistics: | | |
| Resolution (Å) | 2.3 | 2.1 |
| No. of reflections | 7.938 | 10.377 |
| $R_{factor}$[c] | 0.2136 | 0.2111 |
| $R_{free}$[d] | 0.2455(5%)[d] | 0.2360(5%)[d] |
| Number of Atoms: | | |
| Protein | 1362 | 1362 |
| Solvent | 85 | 76 |
| Other (sulfate ion) | 5 | 5 |
| Average B-factors (Å$^2$) | | |
| Protein | 18.4 | 20.8 |
| Solvent | 25.7 | 28.8 |
| R.m.s.d. from ideal geometry: | | |
| Bond lengths (Å) | 0.010 | 0.006 |
| Bond angles (degrees) | 1.12 | 1.11 |
| Ramachandran plot | | |
| Most favored regions (%) | 90.1% | 90.1% |
| Additional allowed regions (%) | 9.9% | 9.2% |
| Generously allowed regions (%) | 0.0% | 0.7% |
| Disallowed regions (%) | 0.0% | 0.0 |

[a]Values in parentheses are for the highest resolution shell
[b]$R_{sym}$ was calculated from $R_{sym} = \Sigma| I_i - <I> |/\Sigma I_i$
[c]$R_{factor}$ for working set of reflections was calculated using: $R_{factor} = \Sigma|| F_o | - | F_c ||/\Sigma| F_o |$
[d]$R_{free}$ for test set and size of test set as % total reflections in parentheses.

It is noted that configuration entropy and disulfide strain predict that RTA 1-33/44-198 V49/E99C should be more stable than RTA 1-33/44-198 R48C/T77C, yet as shown in Table I, these two (SS)RTAs exhibit essentially identical $T_m$ values. This underscores the difficulty of predicting protein stability or designing SS-bonds de novo from geometry or thermodynamic principles alone. In addition to thermodynamic effects, the kinetics of irreversible aggregation likely contributes to the observed increase in Tm for the (SS)RTA variants assayed herein.

Solubility of the Disulfide Variants

Of the nine double mutants constructed (RTA 1-33/44-198 V49C/E99C, RTA 1-33/44-198 R48C/T77C, RTA 1-33/44-198 N141C/I192C, RTA 1-33/44-198 E138C/P143C, RTA 1-33/44-198 L129C/A165C, RTA 1-33/44-198 Q129C/A165C, RTA 1-33/44-198 R125C/A165C, RTA 1-33/44-198 A90C/F108C, and RTA 1-33/44-198 A90C/V111C), seven produced soluble protein in E. coli during an overnight induction period at 17° C. (Table 2), with the protein produced from the double mutants RTA 1-33/44-198 A80C/F98C and RTA 1-33/44-198 L119C/A155C developing in inclusion bodies. The mutations which altered charged residues did not change the calculated pI's by more than 3 pH units, and all of the proteins could be purified by the same protocol.

Antibody Recognition

The locations of the mouse and human neutralizing epitopes have been identified. See Lebeda & Olson (1999) Int. J. Biol. Macromol. 24:19-26; Castelletti et al. (2004) Clin. Exp. Immunol. 136:365-372; Mantis et al. (2006) Infect. Immun. 74:3455-3462; and Neal et al. (2010) Infect. Immun. 78(1):552-561, which are herein incorporated by reference. Immunoblotting To determine if the neutralizing epitope was still intact in the (SS)RTA variants according to the instant invention, an immunoblot containing RTA 1-33/44-198 and RTA 1-33/44-198 variants was probed with a monoclonal mouse antibody, UNIVAX 70/138, which neutralizes ricin toxicity in vitro and in vivo. See Lemley et al. (1994) Hybridoma 13:417-421, which is herein incorporated by reference. An alkaline phosphatase-linked secondary antibody was used to detect the primary antibody. The blot was developed according to manufacture's directions. Specifically, 4 to 5 µg of each of the variants (3 µg of RTA 1-33/44-198 V49C/E99C) was loaded onto the polyacrylamide gel and probed with a monoclonal mouse antibody, UNIVAX 70/138 using methods known in the art. An alkaline phosphatase-linked secondary antibody was used to detect the primary antibody. RTA 1-33/44-198 (1); RTA 1-33/44-198 R48C/T77C (2); RTA 1-33/44-198 V49C/E89C (3); RTA 1-33/44-198 A90C/E99C (4), RTA 1-33/44-198 N141C/I92C (5), RTA 1-33/44-198 R125C/A165C (6), RTA 1-33/44-198 E138C/P143 (7), and RTA 1-33/44-198 Q128C/A165C (8) could be recognized by the antibody, suggesting that the epitope was intact (data not shown).

Figure 3:
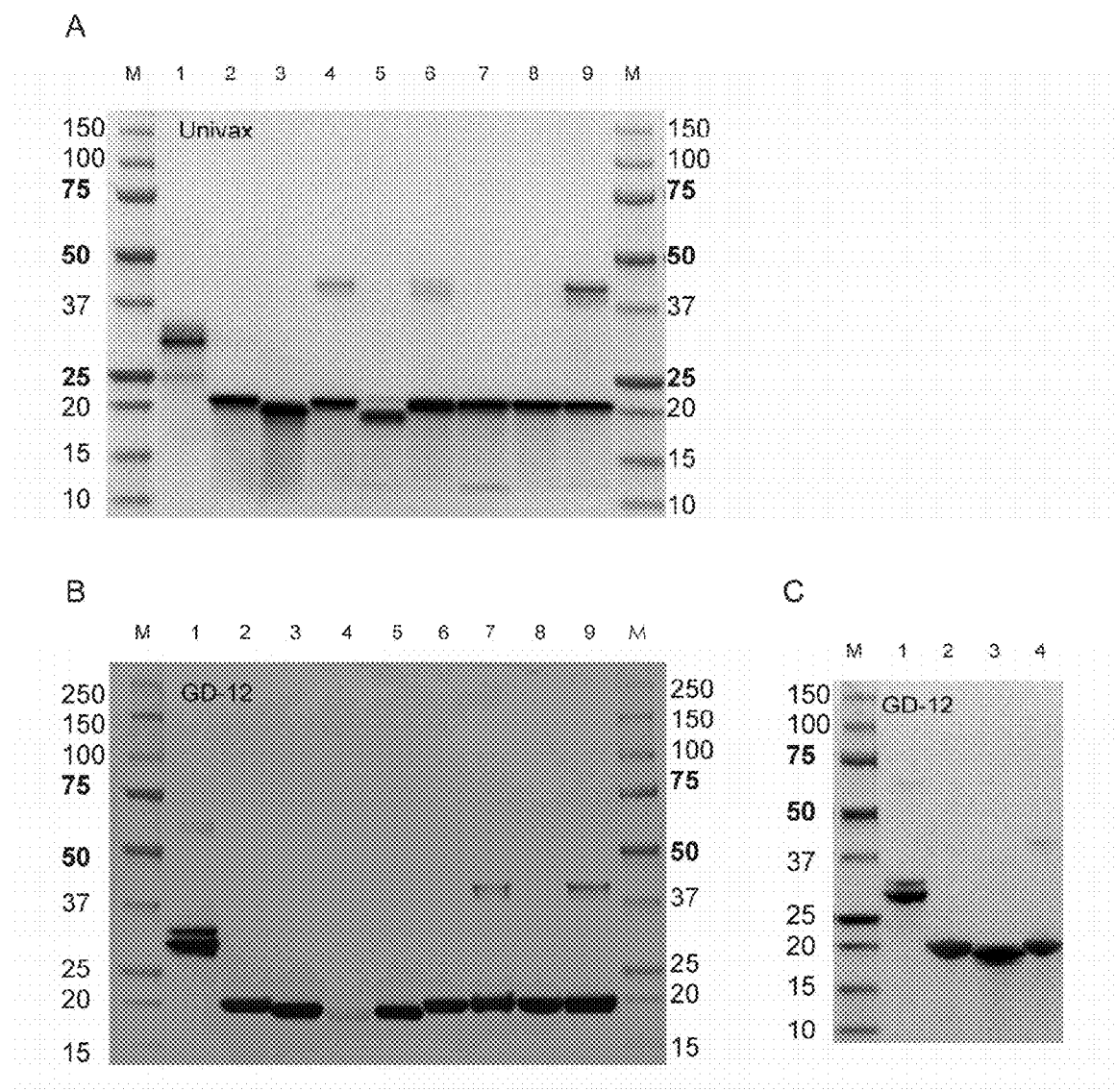
FIG. 3 shows Western blots of various RTA 1-33/44-198 variants described herein. Panel A: 0.25 µg of each variant was loaded into each lane; blot was probed with the murine monoclonal antibody, UNIVAX 70/138. Lanes were loaded as follows: molecular weight marker (M); RTA (1); RTA 1-33/44-198 (2); RTA 1-33/44-198 R48C/T77C (3); RTA 1-33/44-198 V49C/E99C (4); RTA 1-33/44-198 A90C/V111C (5), RTA 1-33/44-198 N141C/I192C (6), RTA 1-33/44-198 R125C/A165C (7), RTA 1-33/44-198 E138C/P143C (8), RTA 1-33/44-198 Q128C/A165C (9). Panel B: 5.0 µg of each variant was loaded into each lane and the blot was probed with a murine MAb, GD12. Lanes were loaded in the same order as in Panel A. The doublet band observed in the RTA control sample results from natural heterogeneity of RTA purified from castor beans, caused partly caused by natural glycosylation. Panel C shows a Western blot using GD12.

The GD-12 antibody, a murine monoclonal antibody specific for RTA residues T161-M175 of RTA, could reproducibly bind the RTA 1-33/44-198 R48C/T77C variant, however reduced staining of the RTA 1-33/44-198V49C/E99C variant was observed. Equal amounts of protein were loaded into the lanes. In one blot, GD-12 did react with RTA 1-33/44-198 V49C/E99C but in the majority of the blots run, GD-12 did not bind the RTA 1-33/44-198 V49C/E99C variant. FIG. 3 shows the Western blots.

Melting Temperatures Monitored by Circular Dichroism

Thermal denaturation of alpha helical regions was monitored by circular dichroism at 222 nm. Denaturation was irreversible and linked to aggregation in 1×PBS pH 7.4, thus thermodynamic parameters could not be calculated. A single sigmoidal transition was observed for each variant in the absence of reducing agents (FIG. 1). As shown in Table 2, two cysteine pairs introduced into RTA 1-33/44-198 had little or no effect on the melting temperature, E138C/P143C and Q118C/A165C, the newly introduced cysteines destabilized the protein suggesting a loss of hydrogen bonding interactions near these cysteines.

$TNB^-$ versus the molar concentration of protein, and the resulting slope yielded the number of free cysteines (Table 2). RTA 1-33/44-198 contains 1 free cysteine, and all of the cysteines are in the reduced state (n=0.97±0.03). The double mutants RTA 1-33/44-198 R48C/T77C and RTA 1-33/44-198 V49C/E99C, which contain 3 cysteines, yielded slopes of 1.00±0.08 and 0.96±0.05, respectively, suggesting that two of the three cysteines were able to form the disulfide bond.

Self Aggregation

In the RTA 1-33/44-198 R48C/T77C double variant the engineered disulfide bond greatly reduce self-aggregation in solution (FIG. 2), which is significant because aggregation has been linked to the irreversible denaturation of protein due to the consequent exposure of hydrophobic residues in solution. In the case of the RTA 1-33/44-198 variants, disulfide bond exchange in the denatured state is also possible as there are 3 cysteines in each of these variants. Sterile-filtered aliquots of each of the mutants were maintained at 37° C. for 61 days. After centrifugation the amount of remaining soluble

TABLE 2

Attempts to Introduce a Stabilizing Disulfide Bond at Different Locations[1] in RTA1-33/44-198

| Ricin Vaccine Immunogen | Solubility/Purity[2] | Number of Free Cys[3] | Apparent $T_m$[4] | Disruption of VLP? |
|---|---|---|---|---|
| RTA 1-33/44-198 | S+/>95% | 0.97 ± 0.03 | 57.9 ± 0.03 | No |
| Substitutions that Increase Apparent Tm | | | | |
| RTA 1-33/44-198 R48C/T77C | S+/>95% | 1.00 ± 0.08 | 62.9 ± 0.22 | No |
| RTA 1-33/44-198 V49C/E99C | S+/>95% | 0.96 ± 0.05 | 62.9 ± 0.21 | No |
| RTA 1-33/44-198 A90C/V111C | S+/>95% | 1.08 ± 0.03 | 60.6 ± 0.24 | No |
| RTA 1-33/44-198 R48C/T77C/D75N | S+/>95% | 1.04 ± 0.02 | 63.2 ± 0.26 | Yes |
| RTA 1-33/44-198 V49C/E99C/V76I | S+/>95% | 0.99 ± 0.03 | 62.6 ± 0.21 | Yes |
| RTA 1-33/44-198 V49C/E99C/D75N | S+/>95% | 1.10 ± 0.06 | 62.2 ± 0.13 | Yes |
| Substitutions with No Effect Apparent Tm | | | | |
| RTA 1-33/44-198 N141C/I192C (SEQ ID NO:23) | S+/>95% | 1.09 ± 0.04 | 59.4 ± 0.53 | No |
| RTA 1-33/44-198 R125C/A165C (SEQ ID NO:24) | 5+/>95% | 2.47 ± 0.01 | 58.2 ± 0.01 | No |
| RTA 1-33/44-198 R48C/T77C/V76I (SEQ ID NO:25) | S+/>95% | 1.89 ± 0.03 | 59.3 ± 0.60 | Yes |
| Substitutions that Reduce Apparent Tm | | | | |
| RTA 1-33/44-198 E138C/P143C (SEQ ID NO:26) | S+/>95% | 1.45 ± 0.07 | 55.9 ± 0.44 | No |
| RTA 1-33/44-198 Q128C/A165C (SEQ ID NO:27) | S+/>95% | 1.88 ± 0.04 | 51.5 ± 0.83 | No |

[1]Presence of desired substitution and no other was confirmed by re-sequencing of entire DNA construct for all variants.

[2]Solubility was assessed qualitatively by evaluating Coomassie blue stained SDS-PAGE gels of initial induction checks. Cells over-expressing recombinant protein were fractionated with scored as I (>50% detected in the insoluble pellet), S (>50% in soluble fraction), or S+ (entirely in soluble fraction). Purity of final product was estimated from Coomassie blue-stained SDS-PAGE. The identity of purified protein was confirmed by reaction with antisera on Western blots.

[3]The number of free Cys residues was quantified for purified proteins by titrating free —SH using 5, 5'-dithiobis-(2-nitrobenzoic acid (DTNB). DTNB titration was conducted in triplicate at five different protein concentrations between 40-50 uM; the mean ±SE was determined from linear regression of the titration plots. Note that the parent protein molecule (RTA1-33/44-198) contains one Cys, whereas each mutant contains a total of three Cys residues. The DTNB assay was optimized to probe the reduced Cys residues such that values significantly greater than one reflect incomplete formation of a stable disulfide bond between the engineered Cys residues.

Thiol titrations yielded stoichiometries greater than 1 (Table 2) for these variants consistent with only partial S—S bond formation. Conversely, S—S bond formation near the truncated RTA loop (33-44) resulted in a significant shift in the measured $T_m$. The measured $T_m$ values of RTA 1-33/44-198 R48C/T77C and RTA 1-33/44-198 V49C/E99C were 5° C. higher than RTA 1-33/44-198. When compared to RTA alone, the $T_m$ values of RTA 1-33/44-198 R48C/T77C and RTA 1-33/44-198 V49C/E99C were approximately 13° C. higher.

Verification of Disulfide Bond Formation

Using DTNB thiol titrations, the number of reduced cysteines in the native proteins were determined to verify the formation of disulfide bonds. The number of reduced cysteines were determined by plotting the molar concentration of protein was measured. 40% of the parent RTA 1-33/44-198 molecule remained soluble after 61 days at 37° C. (phosphate buffered saline, pH 7.4. 1 mg/ml), whereas 66% of RTA 1-33/44-198 R48C/T77C remained soluble after 61 days under identical conditions (FIG. 2). This suggests that it is possible to improve the stability of bacterially produced RTA 1-33/44-198 vaccine immunogen by introduction of a disulfide bond.

Specifically, solutions of each highly purified (>90% purity by PAGE) recombinant immunogen were prepared in PBS pH 7.4 and stored at a fixed starting concentration (0.2-, 1.0-, or 2.0-mg/ml) in a sealed tube at 37° C. For each time point, three separate tubes were sampled, % calculated, and the average %±SE tabulated below. The results are provided in Table 3 as follows:

TABLE 3

Introduction of Disulfide Bond R48C-T77C Extends the Solution Storage Time for RTA1-33/44-198

| Initial Protein Concentration | Days at 37° C. | % Protein Remaining in Solution (mean ± SE) | |
|---|---|---|---|
| | | RTA 1-33/44-198 | RTA 1-33/44-198 R48C/T77C |
| 0.2 mg/ml | 10 | 51 ± 3 | 87 ± 5 |
| | 28 | | 73 ± 5 |
| | 49 | | 59 ± 5 |
| 1.0 mg/ml | 7 | 78 ± 1 | 91 ± 2 |
| | 28 | 51 ± 1 | 72 ± 1 |
| | 61 | 40 ± 1 | 66 ± 1 |
| 2.0 mg/ml | 7 | 71.6 ± 0.3 | 94.5 ± 0.3 |
| | 28 | 45.1 ± 0.6 | 65.7 ± 1.0 |

Compatibility with VLP Site Mutations

A tripeptide, $^{74}L^{75}D^{76}V$ (VLS site), in the ricin A chain has been linked to pulmonary vascular leak syndrome (VLS). See Baluna et al. (1999) PNAS USA 96:3957-3962, which is herein incorporated by reference. Two previously characterized variants, Y80A/D75A and Y80A/V76M do not not result in weight loss (indicative of VLS). See Smallshaw et al. (2002) Vaccine 20:3422-3427; and U.S. Pat. No. 7,829,668, which are herein incorporated by reference. To determine if the disulfide bond could still increase the measured $T_m$ in the presence of either the D75A or V76M mutations, the following triple variants: RTA 1-33/44-198 R48C/T77C/D75N, RTA 1-33/44-198 R48C/T77C/V76I, RTA 1-33/44-198 V49C/E99C/V76I and RTA 1-33/44-198 V49C/E99C/D75N were constructed. Of these variants, only RTA 1-33/44-198 R48C/T77C/V76I was not compatible with the engineered disulfide bond. Incomplete disulfide bond formation was also suggested by the measured number of free cysteine residues. The RTA 1-33/44-198 disulfide variants contain three cysteine residues. The RTA 1-33/44-198 R48C/T77C/V76I variant had 1.89±0.03 titratable cysteines, whereas the other three variants had approximately 1 titratable cysteine and showed similar shifts in their measured $T_m$ values (5° C.) when compared to disulfide-bonded variants. This suggests that (SS) RTA polypeptides according to the instant invention are compatible with the vascular leak site mutations. Thus, in some embodiments, the (SS)RTA polypeptides according to the present invention have a disrupted VLS site, i.e. an amino acid substitution in the VLS site.

Vaccine Studies

The efficacy of the peptides according to the present invention may be determined using methods known in the art. For example, three groups of 20 female BALB/c mice may be treated with i.m. injections of an (SS)RTA, dgRTA (positive control), or phosphate buffered saline (control vehicle). At 0, 4, and 8 weeks, the mice in each group are injected i.m. with 0.1-ml at the following concentration of test/control articles:
 a. Group 1: 20 mice injected with 10 µg of (SS)RTA protein.
 b. Group 2: 10 mice injected with 10 µg of (SS)RTA protein+0.2% alhydrogel.
 c. Group 3: 20 mice injected with 10 µg of dgRTA protein.
 d. Group 4: 20 mice injected with phosphate buffered saline.

At 2 weeks after the third dosing, 20 mice in treatment groups 1, 3, & 4 and 10 mice in treatment group 2 are anesthetized and 0.2 to about 0.3 ml of blood is collected by the periorbital sinus method and recorded. The blood can be later used to measure the specific antibody concentrations and ricin neutralizing antibody titers.

One week after blood collection, the same mice are weighed and ten mice from treatment groups 1, 3, & 4 are injected intraperitoneally on body weight bases with 0.1 ml of a solution that contained 10 mouse $LD_{50}$ of ricin toxin D. The remaining 10 mice from each treatment group are exposed over ten minutes in a dynamic system to a liquid aerosol that supplied 5 to 10 mouse $LD_{50}$ of ricin toxin D. After exposure to ricin, daily cage side observations are made for survival rates.

Serum anti-ricin IgG antibody concentrations may be measured by a direct method ELISA for the detection of ricin-specific IgG immunoglobulin in mouse sera using methods known in the art. Specifically, ricin stock solution (5 mg/ml) (Vector Laboratories, Inc., Burlington, Calif.) is diluted 1:1000 in ELISA coating buffer and 100 µl is added to each well of a plate. The plate is stored at about 12 to about 48 hours at about 4° C. Seven concentrations of mouse anti-ricin serum (Perimmune Inc., Rockville, Md.) are prepared and standardized to provide a suitable standard curve for the ELISA. Positive and negative mouse anti-ricin serum controls are prepared and used. Fresh dilutions of unknown sera are prepared by adding 12.5 µl of serum to 987.5 µl of MASP buffer. Optimal sera dilutions may be determined by conventional methods in the art. The plate is washed 3 times with 0.2 ml/well of ELISA wash buffer. To each well, 200 µl of 5% skim milk buffer is added. The plate is covered and incubated in a moist chamber at about 37° C. for 1 hour. The plate is then washed 3 times with 0.2 ml/well ELISA wash buffer. Then serial dilutions of the unknowns and controls and standards were added to the wells. The plate is incubated at about 37° C. for about 1 hour. The plate is then washed 3 times with 0.2 ml/well ELISA wash buffer. To each well, 100 µl of goat anti-mouse IgG (H+L) conjugate (Kirkegaard & Perry Laboratories, Gaithersburg, Md.) is added and then incubated at room temperature for about 1 hour. The plate is then washed 3 times with 0.2 ml/well ELISA wash buffer. To each well, 100 µl of ABTS peroxidase substrate (Kirkegaard & Perry Laboratories, Gaithersburg, Md.) is added and then allowed to stand at room temperature for about 40 minutes. Then 100 µl of ABTS peroxidase stop solution is added to each well. The plate is read using a microplate reader at 405 nm.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:
1. An isolated polypeptide comprising a first sequence that consists of the amino acid sequence

```
                                                    (SEQ ID NO: 4)
X1X2GLPINQRFILVELSNHAELSVTLAX4X5X6X1NAYVVGYRAGNSX3YFFHPDNQX2DAEAI

THLFTDX3
``` wherein (a) when both X1's are C, the first X2 is V, the second X2 is E, the first X3 is A, the second X3 is V, and X6 is not I, (b) when both X2's are C, the first X1 is R, the second X1 is T, the first X3 is A, and the second X3 is V, or (c) when both X3's are C, the first X1 is R, the second X1 is T, the first X2 is V, and the second X2 is E, X4 is L, F, C, M, A, T, S, W, Y, P, H, E, Q, D, N, K, or R,
X5 is D, I, V, L, F, C, M, A, G, T, S, W, Y, P, H, E, Q, N, K, or R,
X6 is V, I, F, C, M, A, G, T, W, Y, P, H, E, Q, D, N, K, or R.

2. The isolated polypeptide according to claim 1, further comprising a second sequence that consists of the amino acid sequence

```
                                                    (SEQ ID NO: 5)
MIFPKQYPIINFTTAGATVQSYTNFIRAVRGRLTTGADVRHEIPVLPN, (SEQ ID NO: 6)
IFPKQYPIINFTTAGATVQSYTNFIRAVRGRLTTGADVRHEIPVLPN, (SEQ ID NO: 7)
MVPKQYPIINFTTAGATVQSYTNFIRAVRGRLTTGADVRHEIPVLPN, (SEQ ID NO: 8)
MIFPKQYPIINFTTAGATVQSYTNFIRAVRGRLTVLPN, (SEQ ID NO: 9)
MVPKQYPIINFTTAGATVQSYTNFIRAVRGRLTVLPN, (SEQ ID NO: 10)
IFPKQYPIINFTTAGATVQSYTNFIRAVRGRLTVLPN,
or (SEQ ID NO: 11)
IFPKQYPIINFTTAGATVQSYTNFIRAVRGRLTV
``` and/or a third sequence that consists of the amino acid sequence

```
                                                    (SEQ ID NO: 12)
QNRYTFAFGGNYDRLEQLAGNLRENIELGNGPLEEAISALYYYSTGGTQLPTLARSFIICIQMI

SEAARFQYIEGEMRTRIRYNRRS,
or (SEQ ID NO: 13)
QNRYTFAFGGNYDRLEQLAGNLRENIELGNGPLEEAISALYYYSTGGTQLPTLARSFIICIQMIS

EAARFQYIEGEMRTRIRYNRRSA.
```

3. The isolated polypeptide according to claim 2, wherein the second sequence is conjugated to the N-terminus of the first sequence and/or the third sequence is conjugated to the C-terminus of the first sequence.

4. An isolated polypeptide comprising a sequence that consists of the amino acid sequence

```
(SS)RTA198:
                                                    (SEQ ID NO: 14)
IFPKQYPIINFTTAGATVQSYTNFIRAVRGRLTTGADVRHEIPVLPNX1X2GLPINQRFILVELS

NHAELSVTLAX4X5X6X1NAYVVGYRAGNSX3YFFHPDNQX2DAEAITHLFTDX3QNRYTFAFGG

NYDRLEQLAGNLRENIELGNGPLEEAISALYYYSTGGTQLPTLARSFIICIQMISEAARFQYIEG

EMRTRIRYNRRS;
or (SS)RTA1-33/44-198:
                                                    (SEQ ID NO: 15)
IFPKQYPIINFTTAGATVQSYTNFIRAVRGRLTVLPNX1X2GLPINQRFILVELSNHAELSVTLA

X4X5X6X1NAYVVGYRAGNSX3YFFHPDNQX2DAEAITHLFTDX3QNRYTFAFGGNYDRLEQLAG

NLRENIELGNGPLEEAISALYYYSTGGTQLPTLARSFIICIQMISEAARFQYIEGEMRTRIRYNR

RS
``` wherein (a) when both X1's are C, the first X2 is V, the second X2 is E, the first X3 is A, the second X3 is V, and X6 is not I, (b) when both X2's are C, the first X1 is R, the second X1 is T, the first X3 is A, and the second X3 is V, or (c) when both X3's are C, the first X1 is R, the second X1 is T, the first X2 is V, and the second X2 is E, X4 is L, F, C, M, A, T, S, W, Y, P, H, E, Q, D, N, K, or R,
X5 is D, I, V, L, F, C, M, A, G, T, S, W, Y, P, H, E, Q, N, K, or R,
X6 is V, I, F, C, M, A, G, T, W, Y, P, H, E, Q, D, N, K, or R.

5. The polypeptide according to claim 1, wherein the polypeptide retains the functional integrity of the neutralizing immunological epitope of wild type ricin A chain (SEQ ID NO:1), RTA 198 (SEQ ID NO:2), and/or RTA 1-33/44-198 (SEQ ID NO:3).

6. The polypeptide according to claim 1, wherein the polypeptide has an aqueous solubility that is greater than the solubility of wild type ricin A chain (SEQ ID NO:1), RTA 198 (SEQ ID NO:2), and/or RTA 1-33/44-198 (SEQ ID NO:3).

7. A pharmaceutical composition comprising the at least one polypeptide according to claim 1 and a pharmaceutically acceptable vehicle, and optionally an adjuvant.

8. The pharmaceutical composition of claim 7, wherein the composition is capable of eliciting an immune response when administered to a subject.

9. The pharmaceutical composition of claim 8, wherein the immune response is a protective immune response.

10. A vaccine comprising an immunogenic amount of at least one polypeptide according to claim 1.

11. A method of inducing an anti-ricin IgG antibody immune response in a subject which comprises administering to the subject an immunogenic amount of at least one polypeptide according to claim 1.

12. A method of treating, reducing, or inhibiting ricin intoxication in a subject which comprises administering to the subject at least one polypeptide according to claim 1.

13. A kit comprising at least one polypeptide according to claim 1 packaged together with a drug delivery device and optionally instructions for use.

14. The isolated polypeptide of claim 1, wherein when both X1's are C, X5 is D or N and X6 is V, when both X2's are C, X5 is D and X6 is V or I or X5 is N and X6 is V, and when both X3's are C, X5 is D and X6 is V.

15. The isolated polypeptide of claim 4, wherein when both X1's are C, X5 is D or N and X6 is V, when both X2's are C, X5 is D and X6 is V or I or X5 is N and X6 is V, and when both X3's are C, X5 is D and X6 is V.

16. A kit comprising the pharmaceutical composition according to claim 7 packaged together with a drug delivery device and optionally instructions for use.

17. A kit comprising the vaccine according to claim 10 packaged together with a drug delivery device and optionally instructions for use.

* * * * *